(12) United States Patent
Shurgalin et al.

(10) Patent No.: US 9,063,299 B2
(45) Date of Patent: Jun. 23, 2015

(54) TWO-PART SURGICAL WAVEGUIDE

(75) Inventors: Max Shurgalin, Bedford, MA (US);
Vladimir Fuflyigin, Medford, MA (US);
Douglas Woodruff, Stoneham, MA (US); Mihai Ibanescu, Somerville, MA (US); Lori Pressman, Cambridge, MA (US); Charalambos Anastassiou, Malden, MA (US); Soura Bhattacharyya, Cambridge, MA (US); Yoel Fink, Brookline, MA (US)

(73) Assignee: Omni Guide, Inc., Cambridge, MA (US)

( * ) Notice: Subject to any disclaimer, the term of this patent is extended or adjusted under 35 U.S.C. 154(b) by 289 days.

(21) Appl. No.: 13/515,787

(22) PCT Filed: Dec. 13, 2010

(86) PCT No.: PCT/US2010/060109
§ 371 (c)(1),
(2), (4) Date: Nov. 28, 2012

(87) PCT Pub. No.: WO2011/075442
PCT Pub. Date: Jun. 23, 2011

(65) Prior Publication Data
US 2013/0064515 A1 Mar. 14, 2013

Related U.S. Application Data

(60) Provisional application No. 61/286,676, filed on Dec. 15, 2009.

(51) Int. Cl.
*G02B 6/02* (2006.01)
*G02B 6/36* (2006.01)
(Continued)

(52) U.S. Cl.
CPC ............ *G02B 6/3624* (2013.01); *G02B 6/102* (2013.01); *A61B 18/203* (2013.01);
(Continued)

(58) Field of Classification Search
CPC ............ A61B 18/22; A61B 2018/2227; A61B 18/20; A61B 18/201; A61B 18/2015; A61B 18/203; G02B 6/023; G02B 6/02304; G02B 6/032; G02B 6/10; G02B 6/102
USPC .......................................... 385/115–121, 125
See application file for complete search history.

(56) References Cited

U.S. PATENT DOCUMENTS 3,467,098 A 9/1969 Ayers
3,659,915 A 5/1972 Maurer et al.
(Continued)

FOREIGN PATENT DOCUMENTS

EP 0589468 A2 3/1994
EP 0 844 501 A2 5/1998
(Continued)

OTHER PUBLICATIONS

"Hollow Fibers for Infrared Laser Light Transmission", Hitachi Cable Review No. 23, Aug. 2004.
(Continued)

*Primary Examiner* — Ryan Lepisto
*Assistant Examiner* — Guy Anderson
(74) *Attorney, Agent, or Firm* — Douglas E. Denninger

(57) ABSTRACT

An apparatus includes a light source configured to provide radiation at a wavelength and a conduit configured to direct radiation at a wavelength from the light source to a target location of a patient. The conduit includes a first optical waveguide extending along a waveguide axis, the first optical waveguide being a flexible waveguide having a hollow core, the first optical waveguide being configured to guide the radiation at through the core along the waveguide axis; and a second optical waveguide extending along the waveguide axis, the second optical waveguide having a hollow core and being coupled to the first optical waveguide to receive the radiation from the first optical waveguide and to deliver the radiation to the target location. The first optical waveguide is a photonic crystal fiber and the second optical waveguide is not a photonic crystal fiber waveguide.

25 Claims, 14 Drawing Sheets

(51) Int. Cl.
  *G02B 6/10* (2006.01)
  *A61B 18/20* (2006.01)
  *A61B 18/22* (2006.01)
  *G02B 6/032* (2006.01)
  *G02B 6/24* (2006.01)

(52) U.S. Cl.
  CPC ...... *A61B 2018/2227* (2013.01); *A61B 18/201* (2013.01); *A61B 18/20* (2013.01); *G02B 6/023* (2013.01); *G02B 6/10* (2013.01); A61B 18/22 (2013.01); *A61B 2018/2222* (2013.01); *G02B 6/02304* (2013.01); *G02B 6/032* (2013.01); *G02B 6/241* (2013.01)

(56) References Cited

U.S. PATENT DOCUMENTS

| | | |
|---|---|---|
| 3,858,577 A | 1/1975 | Bass et al. |
| 3,920,980 A | 11/1975 | Nath |
| 4,076,380 A | 2/1978 | DiMarcello et al. |
| 4,099,835 A | 7/1978 | French et al. |
| 4,170,997 A | 10/1979 | Pinnow et al. |
| 4,583,526 A | 4/1986 | Ali |
| 4,652,083 A | 3/1987 | Laakmann |
| 4,672,969 A | 6/1987 | Dew |
| 4,688,892 A | 8/1987 | Laakmann |
| 4,688,893 A | 8/1987 | Laakmann |
| 4,805,987 A | 2/1989 | Laakmann et al. |
| 4,806,289 A | 2/1989 | Laursen et al. |
| 4,911,712 A | 3/1990 | Harrington |
| 4,913,505 A | 4/1990 | Levy |
| 4,917,084 A | 4/1990 | Sinofsky |
| 4,930,863 A | 6/1990 | Croitoriu et al. |
| 4,932,749 A | 6/1990 | Haidle et al. |
| 4,947,540 A | 8/1990 | Komachi |
| 5,002,051 A | 3/1991 | Dew et al. |
| 5,005,944 A | 4/1991 | Laakmann et al. |
| 5,030,217 A | 7/1991 | Harrington |
| 5,044,717 A | 9/1991 | Levatter |
| 5,061,265 A | 10/1991 | Abela et al. |
| 5,062,842 A | 11/1991 | Tiffany |
| 5,071,222 A | 12/1991 | Laakmann et al. |
| 5,097,525 A | 3/1992 | Garcia et al. |
| 5,136,676 A | 8/1992 | Arnett et al. |
| 5,139,494 A | 8/1992 | Freiberg |
| 5,140,984 A | 8/1992 | Dew et al. |
| 5,147,354 A | 9/1992 | Boutacoff et al. |
| 5,163,935 A | 11/1992 | Black et al. |
| 5,257,991 A | 11/1993 | Fletcher et al. |
| 5,276,761 A | 1/1994 | Shimoyama et al. |
| 5,288,288 A | 2/1994 | Lewis et al. |
| 5,304,171 A | 4/1994 | Gregory et al. |
| 5,312,398 A | 5/1994 | Hobart et al. |
| 5,325,458 A | 6/1994 | Morrow et al. |
| 5,354,294 A | 10/1994 | Chou |
| 5,380,317 A | 1/1995 | Everett et al. |
| 5,423,805 A | 6/1995 | Brucker et al. |
| 5,437,660 A | 8/1995 | Johnson et al. |
| 5,440,664 A | 8/1995 | Harrington et al. |
| 5,470,330 A | 11/1995 | Goldenberg et al. |
| 5,471,553 A | 11/1995 | Teshima |
| 5,480,050 A | 1/1996 | Morrow et al. |
| 5,486,171 A | 1/1996 | Chou |
| 5,489,256 A | 2/1996 | Adair |
| 5,497,440 A | 3/1996 | Croitoru et al. |
| 5,497,441 A | 3/1996 | Croitoru et al. |
| 5,498,260 A | 3/1996 | Rink et al. |
| 5,558,668 A | 9/1996 | Lankford et al. |
| 5,567,471 A * | 10/1996 | Harrington et al. ........ 427/163.2 |
| 5,573,531 A | 11/1996 | Gregory |
| 5,630,807 A | 5/1997 | Joffe |
| 5,643,175 A | 7/1997 | Adair |
| 5,729,646 A | 3/1998 | Miyagi et al. |
| 5,735,844 A | 4/1998 | Anderson et al. |
| 5,784,400 A | 7/1998 | Joannopoulos et al. |
| 5,815,627 A | 9/1998 | Harrington |
| 5,824,023 A | 10/1998 | Anderson |
| 5,830,209 A | 11/1998 | Savage et al. |
| 5,843,073 A | 12/1998 | Sinofsky |
| 5,893,828 A | 4/1999 | Uram |
| 5,935,491 A | 8/1999 | Tripathy et al. |
| 5,951,543 A * | 9/1999 | Brauer ............................ 606/10 |
| 5,995,696 A | 11/1999 | Miyagi et al. |
| 6,104,853 A | 8/2000 | Miyagi et al. |
| 6,130,780 A | 10/2000 | Joannopoulos et al. |
| 6,141,476 A | 10/2000 | Matsuura et al. |
| 6,165,205 A | 12/2000 | Neuberger |
| 6,172,810 B1 | 1/2001 | Fleming et al. |
| 6,306,130 B1 | 10/2001 | Anderson et al. |
| 6,343,174 B1 | 1/2002 | Neuberger |
| 6,404,966 B1 | 6/2002 | Kawanishi et al. |
| 6,463,200 B2 | 10/2002 | Fink et al. |
| 6,496,632 B2 | 12/2002 | Borrelli et al. |
| 6,527,764 B1 | 3/2003 | Neuberger et al. |
| 6,547,780 B1 | 4/2003 | Sinofsky |
| 6,563,981 B2 | 5/2003 | Weisberg et al. |
| 6,571,045 B2 | 5/2003 | Hasegawa et al. |
| 6,603,911 B2 | 8/2003 | Fink et al. |
| 6,606,440 B2 | 8/2003 | Hasegawa et al. |
| 6,625,364 B2 | 9/2003 | Johnson et al. |
| 6,683,277 B1 | 1/2004 | Millard et al. |
| 6,723,090 B2 | 4/2004 | Altshuler et al. |
| 6,728,439 B2 | 4/2004 | Weisberg et al. |
| 6,735,369 B2 | 5/2004 | Komachi et al. |
| 6,788,864 B2 | 9/2004 | Ahmad et al. |
| 6,801,698 B2 | 10/2004 | King et al. |
| 6,816,243 B2 | 11/2004 | Shurgalin et al. |
| 6,856,742 B2 | 2/2005 | Broeng et al. |
| 6,879,386 B2 | 4/2005 | Shurgalin et al. |
| 6,895,154 B2 | 5/2005 | Johnson et al. |
| 6,898,359 B2 | 5/2005 | Soljacic et al. |
| 6,903,873 B1 | 6/2005 | Joannopoulos et al. |
| 6,985,661 B1 | 1/2006 | Russell et al. |
| 6,986,739 B2 | 1/2006 | Warren et al. |
| 7,042,631 B2 | 5/2006 | Smith et al. |
| 7,072,553 B2 | 7/2006 | Johnson et al. |
| 7,099,533 B1 | 8/2006 | Chenard |
| 7,142,756 B2 | 11/2006 | Anderson et al. |
| 7,167,622 B2 * | 1/2007 | Temelkuran et al. ......... 385/123 |
| 7,190,875 B2 | 3/2007 | Anderson et al. |
| 7,231,122 B2 | 6/2007 | Weisberg et al. |
| 7,272,285 B2 | 9/2007 | Benoit et al. |
| 7,310,466 B2 | 12/2007 | Fink et al. |
| 7,311,962 B2 | 12/2007 | Fink et al. |
| 7,331,954 B2 * | 2/2008 | Temelkuran et al. ............ 606/15 |
| 7,349,589 B2 * | 3/2008 | Temelkuran et al. ............ 385/11 |
| 8,280,212 B2 | 10/2012 | Goell et al. |
| 8,320,725 B2 | 11/2012 | Temelkuran et al. |
| 2002/0150364 A1 | 10/2002 | Bassett et al. |
| 2002/0193781 A1 | 12/2002 | Loeb |
| 2003/0044158 A1 | 3/2003 | King et al. |
| 2004/0068256 A1 | 4/2004 | Rizoiu et al. |
| 2004/0137168 A1 | 7/2004 | Fuflyigin |
| 2004/0141702 A1 | 7/2004 | Fuflyigin et al. |
| 2005/0008291 A1 | 1/2005 | Baney |
| 2006/0052661 A1 | 3/2006 | Gannot et al. |
| 2006/0201206 A1 | 9/2006 | Benoit et al. |
| 2007/0122096 A1 * | 5/2007 | Temelkuran et al. ......... 385/126 |
| 2008/0177257 A1 * | 7/2008 | Smith et al. .................... 606/15 |
| 2009/0034927 A1 | 2/2009 | Temelkuran et al. |
| 2009/0204111 A1 | 8/2009 | Bissig et al. |
| 2011/0224661 A1 | 9/2011 | Gille et al. |

FOREIGN PATENT DOCUMENTS

| | | |
|---|---|---|
| GB | 1198904 A | 7/1970 |
| GB | 2288469 A | 10/1995 |
| JP | 2003222740 A | 8/2003 |
| WO | WO-8501445 A1 | 4/1985 |
| WO | WO-9900062 A1 | 1/1999 |
| WO | WO-99/47465 A1 | 9/1999 |
| WO | WO-00/22466 A1 | 4/2000 |
| WO | WO-00/43815 A1 | 7/2000 |
| WO | WO-00/46287 A1 | 8/2000 |

(56) References Cited

FOREIGN PATENT DOCUMENTS

| WO | WO-02/41050 | A2 | 5/2002 |
|---|---|---|---|
| WO | WO-0261467 | A2 | 8/2002 |
| WO | WO-0272489 | A2 | 9/2002 |
| WO | WO-03050571 | A2 | 6/2003 |
| WO | WO-03079073 | A1 | 9/2003 |
| WO | WO-03079077 | A1 | 9/2003 |
| WO | WO-2004052078 | A2 | 6/2004 |
| WO | WO-2004058328 | A2 | 7/2004 |
| WO | WO-2004064623 | A2 | 8/2004 |

OTHER PUBLICATIONS

Allan et al. "Photonic crystal fibers: effective-index and band-gap guidance." Photonic Crystals and Light Localization in the 21st Century. 2001: Kluwer. pp. 305-320.

Anastassiou, C. et al., "Fiber Deliver CO2 Laser Beams for Medical Applications", Mar. 1, 2004, Photonics Spectra.

Barkou et al. "Silica-air photonic crystal fiber design that permits wave guiding by a true photonic bandgap effect." Optics Letters, 24:1, Jan. 1, 1999, pp. 46-48.

Baumeister, P. "The transmission and degree of polarization of quarter-wave stacks at non-normal incidence." Opt. Acta, 8, 1961, pp. 105-119.

Birks et al. "Full 2-D photonic bandgaps in silica/air structures." Electronic Letters, 31:22, Oct. 26, 1995, pp. 1941-1943.

Bormashenko et al. "Development of new-near-infrared filters based on the 'sandwich' polymerchalcogenide glass-polymer composites." Optical Engineering, 40:5,2001, pp. 661-662.

Bormashenko et al. "New Oriented Polymer/Thermoplastic Glass Composites for IR Optics." Engineering Materials, 10, 2000, pp. 657-658.

Bormashenko et al. "Optical Properties and infrared optics applications of composite films based on EJ polyethylene and low-melting-point chalcogendie." Society of Photo-Optical Instrumentation Engineers, Feb. 2002. pp. 295-302.

Bornstein et al. "Chalcogenide Hollow Fibers." Journal of Non-Crystalline Solids, 77:8, 1985, pp. 1277-1280.

Broeng et al. "Analysis of air-guiding photonic bandgap fibers." Optics Letters, 25:2, 2000, pp. 96-98.

C. Charlton et al., in IEEE Proc.-Optoelectron., vol. 150, No. 4, pp. 306-309.

Cregan et al. "Single-Mode Photonic Band Gap Guidance of Light in Air." Science, 285, Sep. 3, 1999, pp. 1537-1539.

Dai et al. "High-peak-power, pulsed CO2 laser light delivery by hollow glass waveguides." Appl Optics, 36, 1997, pp. 5072-5077.

De Boor, Carl, Applied Mathematical Sciences: A Practical Guide to Splines, 1978, Springer-Verlag, New York, United States.

De Sterke et al. "Differential losses in Bragg fibers." J. Appl. Phys., 76:2, Jul. 15, 1994, pp. 680-688.

E. Hartouni et al., "Progress in IR optical fibers", SPIE, 1984, pp. 131-140, vol. 505, Advances in Optical Materials, General Dynamics, Pomona, California.

Eggleton et al. Microstructured optical fiber devices. Optics Express, 9:13,2001, pp. 698-713.

European Search Report for Application No. / Patent No.-03796927.6 / PCT/US0339344, dated May 12, 2006.

Feigel A. et al. "Chalcogenide glass-based three-dimensional photonic crystals." Applied Physics Letters, 77:20, pp. 3221-3223, Nov. 13, 2000.

Fink et al. "A dielectric omnidirectional reflector." Science, 282:5394, 1998, pp. 1679-1682.

Fink et al. "Guiding Optical Light in Air Using an All-Dielectric Structure." Journal of Lightwave Technology, 17:11,Nov.II, 1999,pp. 2039-2041.

Fitt et al. "Modeling the fabrication of hollow fibers: Capillary drawings." Journal of Lightwave; Technology, 19: 12, 2001, pp. 1924-1931.

Fletcher, C. A. J., Computational Galerkin Methods: With 107 Figures, 1984, Springer-Verlag, New York, United States.

Gopal et al. "Deposition and characterization of metal sulfide dielectric coatings for hollow glass waveguide." Optical Society of America, 2003. Optics Express, 11:24, Dec. 1, 2003.

Harrington, J.A. "Infrared Fibers in Handbook of Optics." McGraw-Hill, 2001, pp. 14, 1-14, 13.

Harrington, James. "A Review ofiR Transmitting, Hollow Waveguides." Fiber and Integrated Optics, 19, 2000, pp. 211-217.

Hart et al. "External Reflection from Omnidirectional Dielectric Mirror Fibers." Science, 296, Apr. 19, 2002, pp. 510-513.

Hilton, A.R., "Optical Properties ofChalcogenide Glasses." Journal ofNon-Crystalline Solids, 2, 1970, pp. 28-39.

Hongo et al. "Transmission of Kilowatt-Class Co2-Laser Light through Dielectric-Coated Metallic Hollow Wave-Guides for Material Processing." Applied Optics, 31:24, 1992. pp. 5114-5120.

Hongo et al., "Infrared Hollow Fibers for Medical Applications", Hitachi Cable Review No. 23, Aug. 2004.

Ibanescu et al. "An all-dielectric coaxial waveguide." Science, 289:5478,2000, pp. 415-419.

Ibanescu et al. "Analysis of Mode Structure in OmniGuide Fibers." Physical Review E, 67:4, 2003.

International Search Report for PCT/US20061007437 by Mildred Condon and W. Elflein dated Jul. 13, 2006.

International Search Report, 10127105, PCT/US05112047.

Ivanenko et al. "In vitro incision of bone tissue with a Q-switch C02 laser. Histological examination." Lasers in the Life Sciences, vol. 9, pp. 171-179 (2000).

Joannopoulos et al., Photonic Crystals by (Princeton University Press, Princeton, NJ 1995).

John F. Ready "4.8 Process Gas Nozzles—Chapter 4: Components for Laser Materials Processing Systems" LIA Handbook of Laser Materials Processing, pp. 155-159 (2001).

John, S. "Strong Localization of Photons in Certain Disordered Dielectric Superlattices." Physical Review Letters, 58:23, 1987, pp. 2486-2489.

Johnson et al. "Low-loss asymptotically single-mode propagation in large-core OmniGuide fibers." Optics Express, 9:13,2001, pp. 748-779.

Keck et al. "On the ultimate lower limit of attenuation in glass optical waveguides." Applied Physics Letters, 22:7, 1973, pp. 307-309.

King et al. "Laboratory preparation of highly pure As2Se3 glass." J. Non-Cryst. Sol., 181, 1995, pp. 231-237.

Knight et al. "Photonic Band Gap Guidance in Optical Fibers." Science, 282, Nov. 20, 1998, pp. 1476-1478.

Kucuk et al. "An estimation of the surface tension for silicate glass melts at 1400° C. using statistical analysis." Glass Techno!., 40, 1999, pp. 149-153.

Mahlein. Generalized Brewster-angle conditions for quarter-wave multilayers at non-normal incidence. J. Opt. Soc. Am., 64, 1974, pp. 647-653.

Marcatilli et al. "Hollow metallic and dielectric waveguides for long distance optical transmission and lasers." Bell Syst. Tech. J., 43, 1964, pp. 1783-1809.

Matsuura et al. "Hollow infrared fibers fabricated by glass-drawing technique." Optics Express, 10: 12, 2002, pp. 488-492.

Matsuura et al. "Small-bore hollow waveguide for delivery of near single mode IR laser radiation." Electronic Letters, 30, 1994, pp. 1688-1690.

Mitra et al. "Nonlinear limits to the information capacity of optical fibre communications." Nature, 411,2001, pp. 1027-1030.

Miyagi et al. "Design Theory of Dielectric-Coated Circular Metallic Waveguides for Infrared Transmission." Journal of Lightwave Technology, 2:2, 1984, pp. 116-126.

Monro, T.M. et al. "Chalcogenide Holey Fibres." Electronics Letters, 36:24, pp. 1998-2000, Nov. 23, 2000.

Mossadegh R. et al. "Fabrication of single-mode chalcogenide optial fiber." Journal of Lightwave Technology, 16:2, pp. 214-216, Feb. 1998.

Nishii, J. et al. "Chalcogenide glass fiber with a core-cladding structure." Applied Optics, 28: 23, pp. 5122-5127, Dec. 1, 1989.

Nubling et al. "Hollow-waveguide delivery systems for high-power, industrial C02 lasers." Applied Optics, 34:3, Jan. 20, 1996, pp. 372-380.

(56) References Cited

OTHER PUBLICATIONS

Ouyang et al. "Comparative study of air-core and coaxial Bragg fibers: single-mode transmission and dispersion characteristics." Optics Express, 9:13, 2001, pp. 733-747.

Pottage et al. "Robust photonic band gaps for hollow core guidance in PCF made from high index glass." Optics Express, 11:22, Nov. 3, 2003, pp. 2854-2861.

Press, William H. et al., Numerical Recipes in FORTRAN: The Art of Scientific Computing Second Edition, 1992, Press Syndicate of the University of Cambridge, New York, United States.

Renn et al. "Laser-Guided Atoms in Hollow-Core Optical Fibers." Physical Review Letters, 75:18, 1995, pp. 3253-3256.

Rundquist et al. "Phase-matched generation of coherent soft-X-rays." Science, 280:5368, 1998, pp. 1412-1415.

Sanghera et al. "Active and passive chalcogenide glass optical fibers for IR applications: a review." Journal of Non-Crystalline Solids, 257, 1999, pp. 6-16.

Sanghera et al. "Development and Infrared Applications of Chalcogenide Glass Optical Fibers." Fiber and Integrated Optics, 19:251, 2000, pp. 251-274.

Sanghera, J.S. et al. "Fabrication of long lengths of low-loss IR transmitting AS4OS (60-X) sex glass fibers." Journal of Lightwave Technology, 14:5, pp. 743-748, May 1, 1996.

Seddon, A.B. "Chalcogenide glasses: a review of their preparation, properties and applications." J. Non-Cyrst. Sol., 184, 1995, pp. 44-50.

Skorobogatiy M. et al., Geometric variations in high index-contrast waveguides, coupled mode theory in curvilinear coordinates, Optics Express, Oct. 21, 2002, pp. 1227-1243, vol. 10, No. 21.

Temelkuran et al. "Low-loss infrared dielectric materials system for broadband dual-rang omnidirectional reflectivity." Optics Letters, 26, 2001, pp. 1370-1372.

Temelkuran et al. "Wavelength-scalable hollow optical fibres with large photonic bandgaps for C02 laser transmission." Nature, 420, Dec. 12, 2002, pp. 650-653.

Torres et al. "OmniGuide Photonic Bandgap Fibers for flexible Delivery of C02 Lasers in Laryngology" Proceedings of SPIE, vol. 5686, pp. 310-321 (Apr. 2005).

Varsheneya A.K. Fundamentals of Inorganic Glasses, Academic Press, San Diego, pp. 5-7, 1994.

Varshneya, A. K. "Some comments on physical properties of chalcogenide glasses." J. Non-Cryst. Sol., 273, 2000, pp. 1-7.

Vienne et al. "First demonstration of air-silica Bragg fiber." Optical Society of America, 2003. Institute of Electrical and Electronics Engineers. Optical Fiber Communication Conference and Exposition Postdeadline Papers.

Voight B. et al., Optical Glasses for Infrared Transmittance: Synthesis and Properties of Chalcogenide Glasses, Physics and Applications of Non-Crystalline Semiconductors in Optoelectronics, 1997, pp. 155-169, Kluwer Academic Publishers, Netherlands.

Weber et al. Giant Birefringent Optics in Multilayer Polymer Mirrors. Science, 287, 2000, pp. 2451-2456.

Winn et al. Omnidirectional reflection from a one-dimensional photonic crystal. Optics Letters, 23, 1998, pp. 1573-1575.

Yablonovitch. E. "Inhibited Spontaneous Emission in Solid-State Physics and Electronics." Physical Review Letters, 58:20, 1987, pp. 2059-2062.

Yeh et al. "Theory of Bragg Fiber." Journal of the Optical Society of America, 68:9, 1978, pp. 1196-1201.

Yeh et al. Electromagnetic propagation in periodic stratified media. I. General theory. J. Opt. Soc. Am., 67, 1977, pp. 423-438.

PCT International Search Report and Written Opinion mailed Feb. 3, 2011 in corresponding Application No. PCT/US2010/060109 filed Dec. 13, 2010.

* cited by examiner

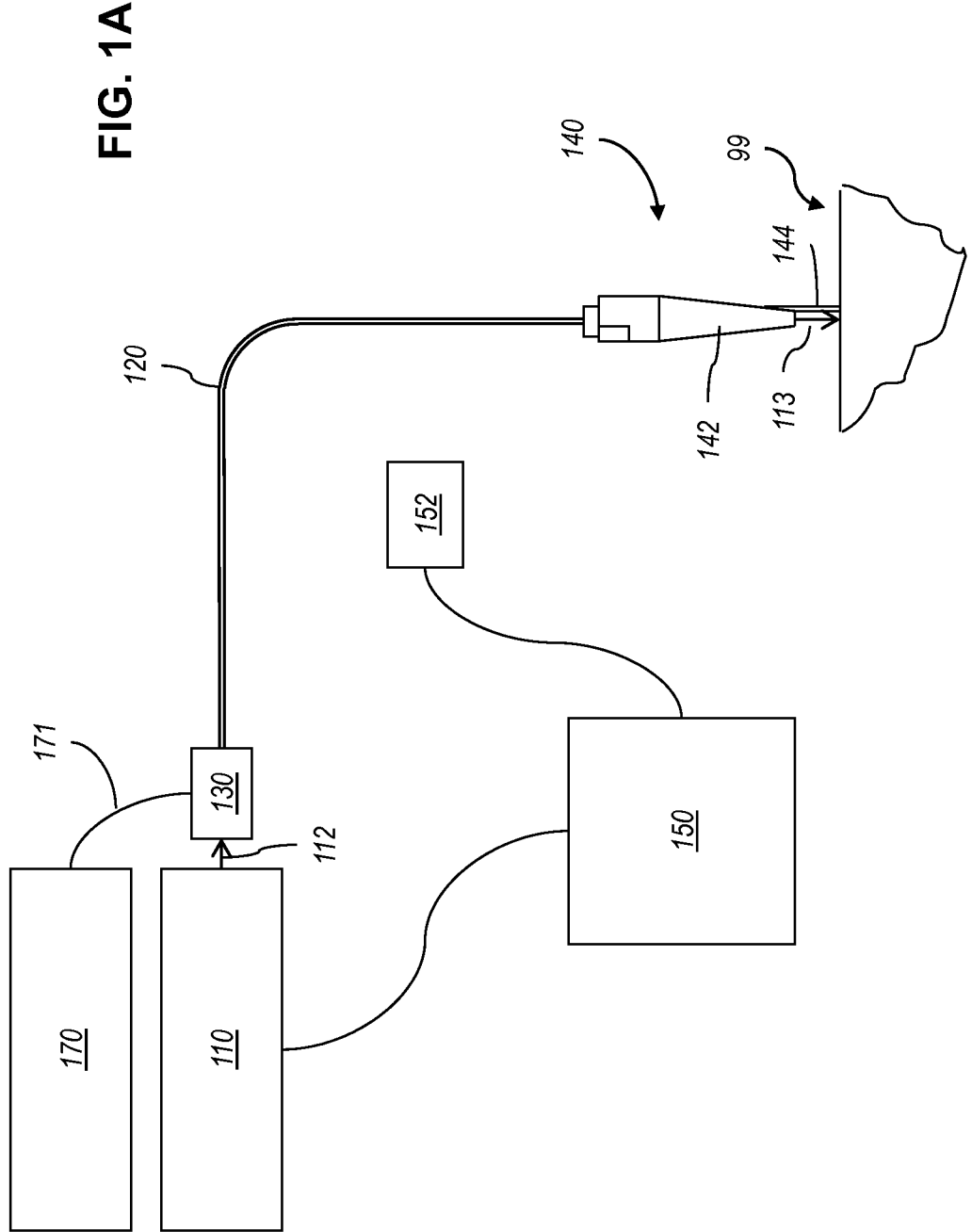

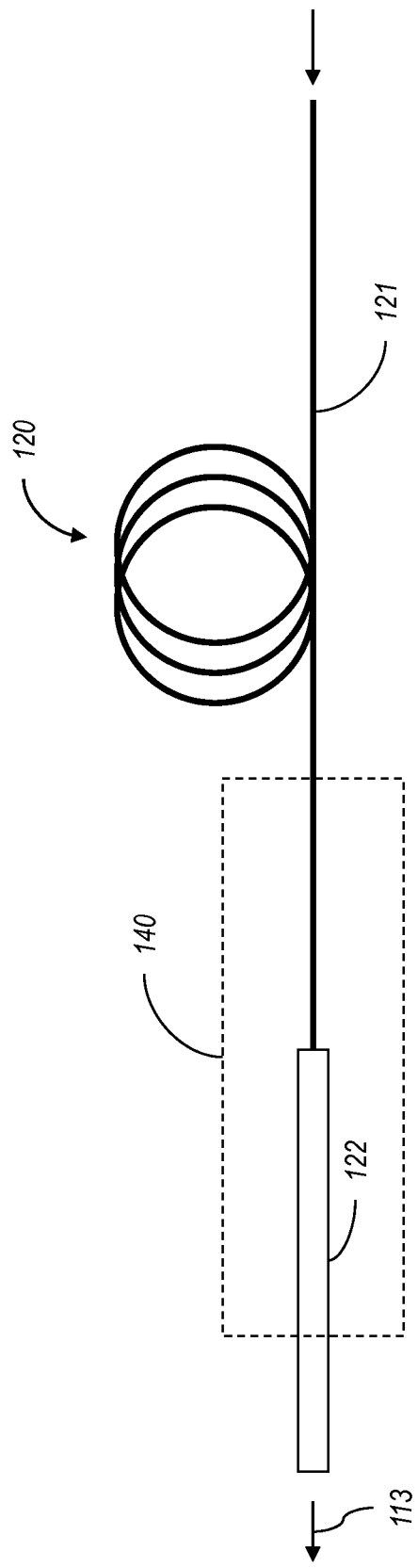

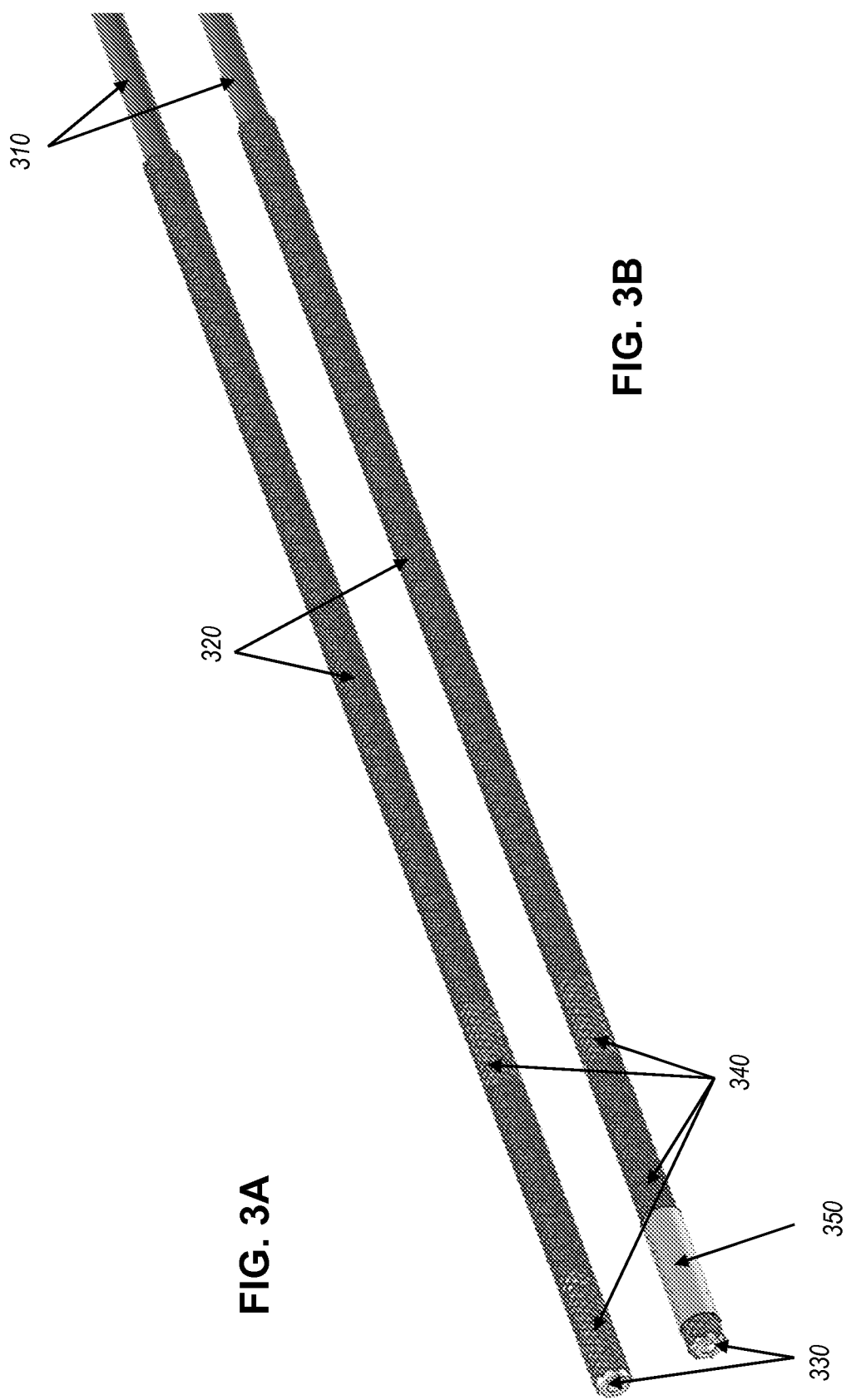

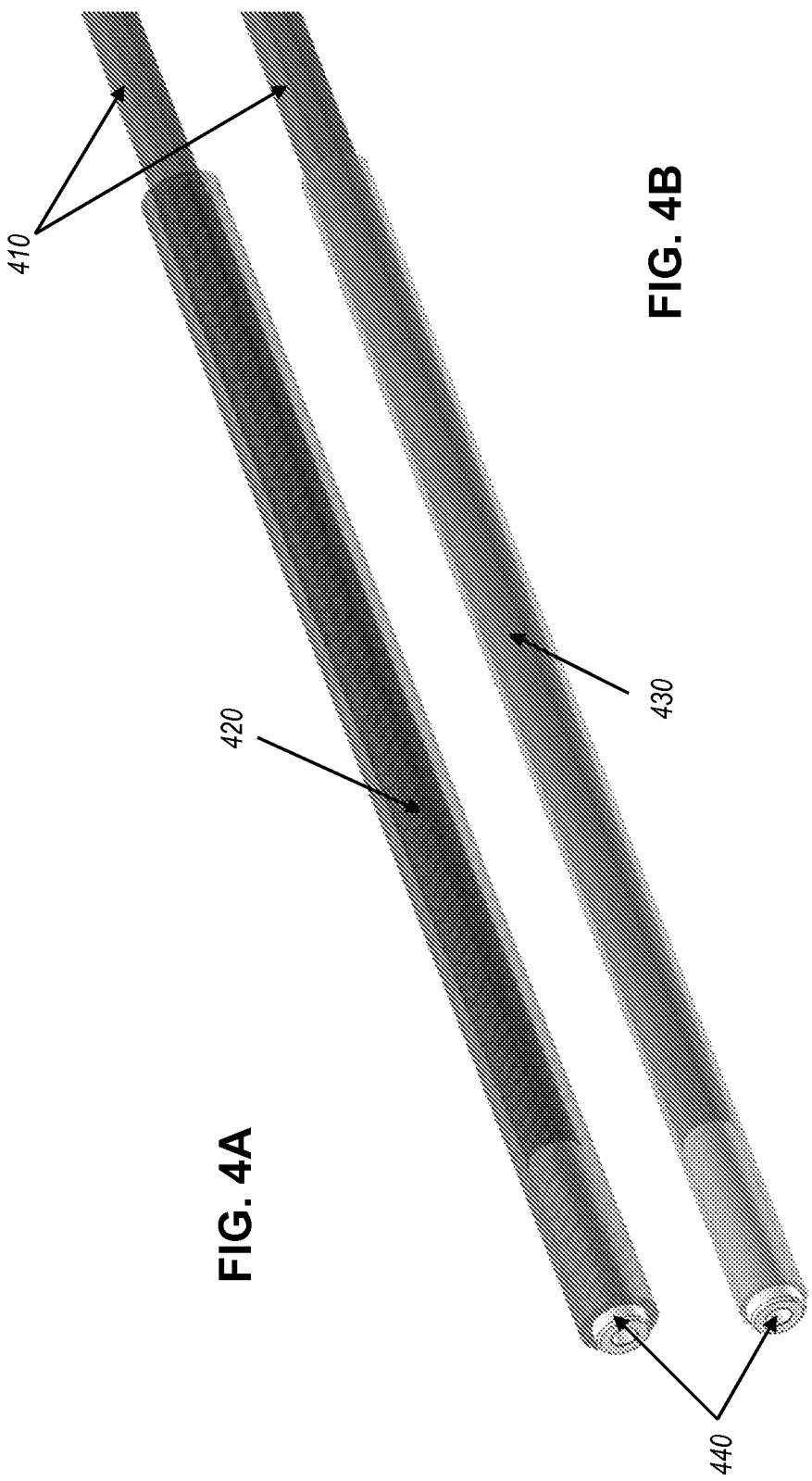

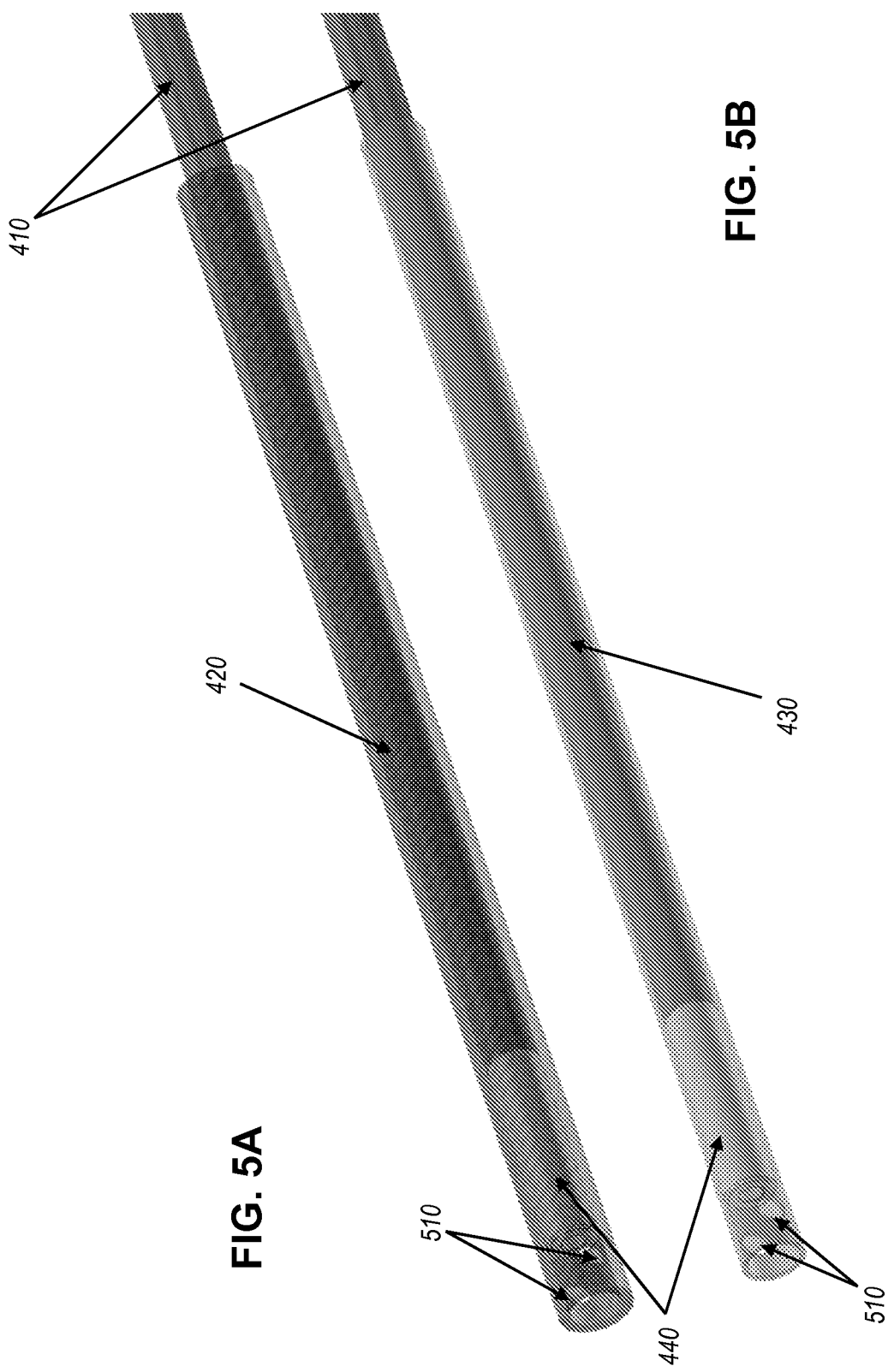

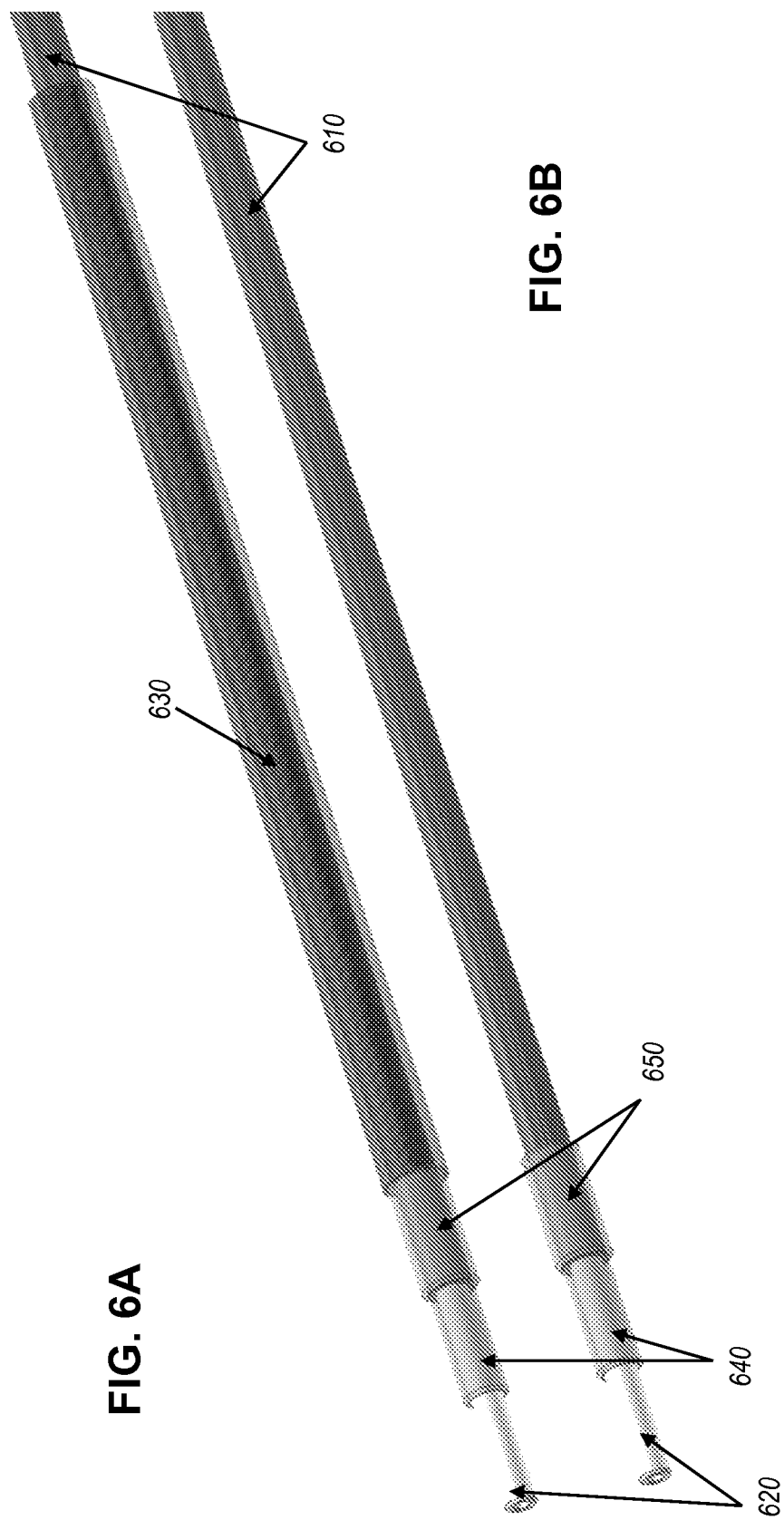

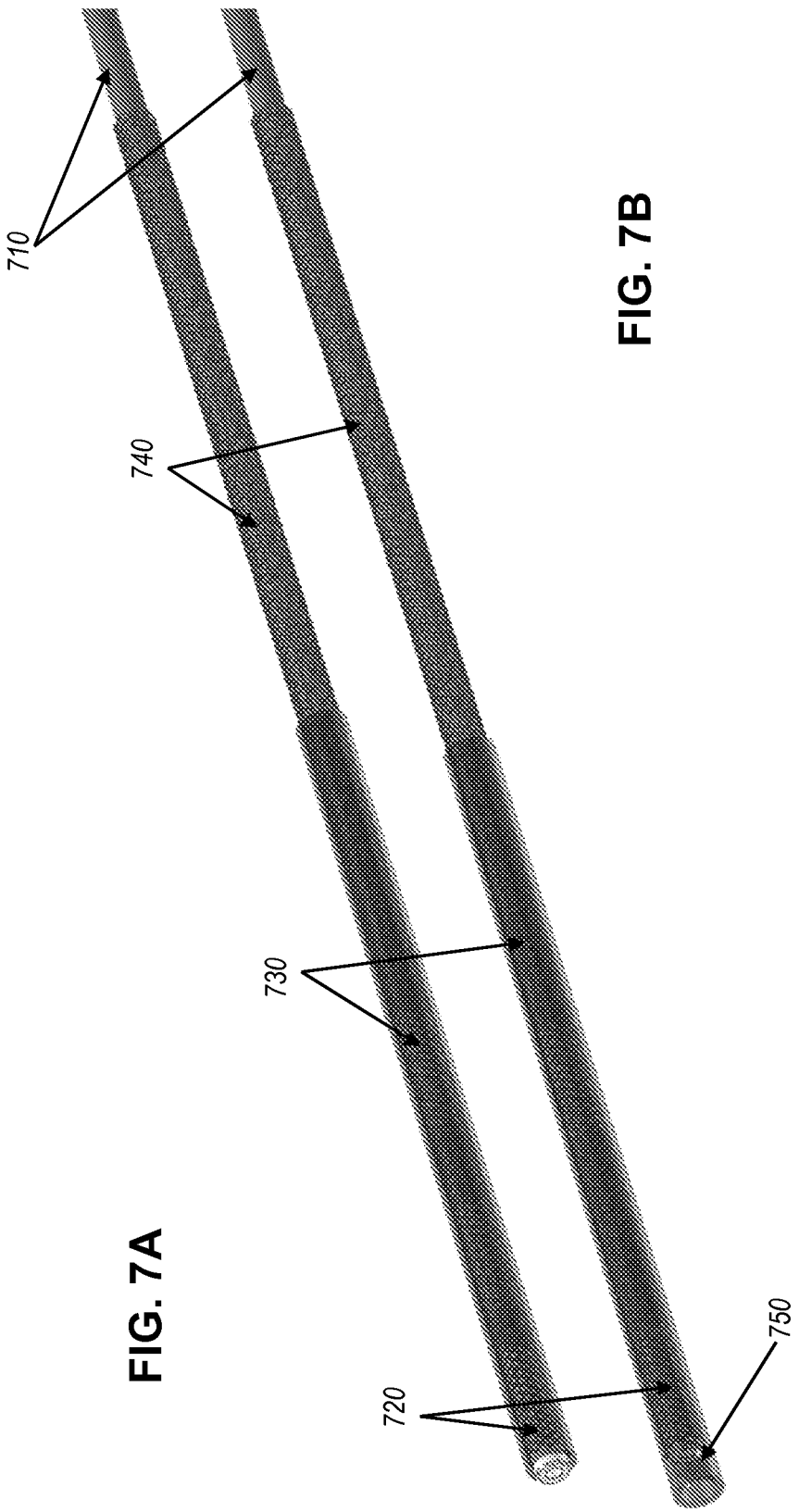

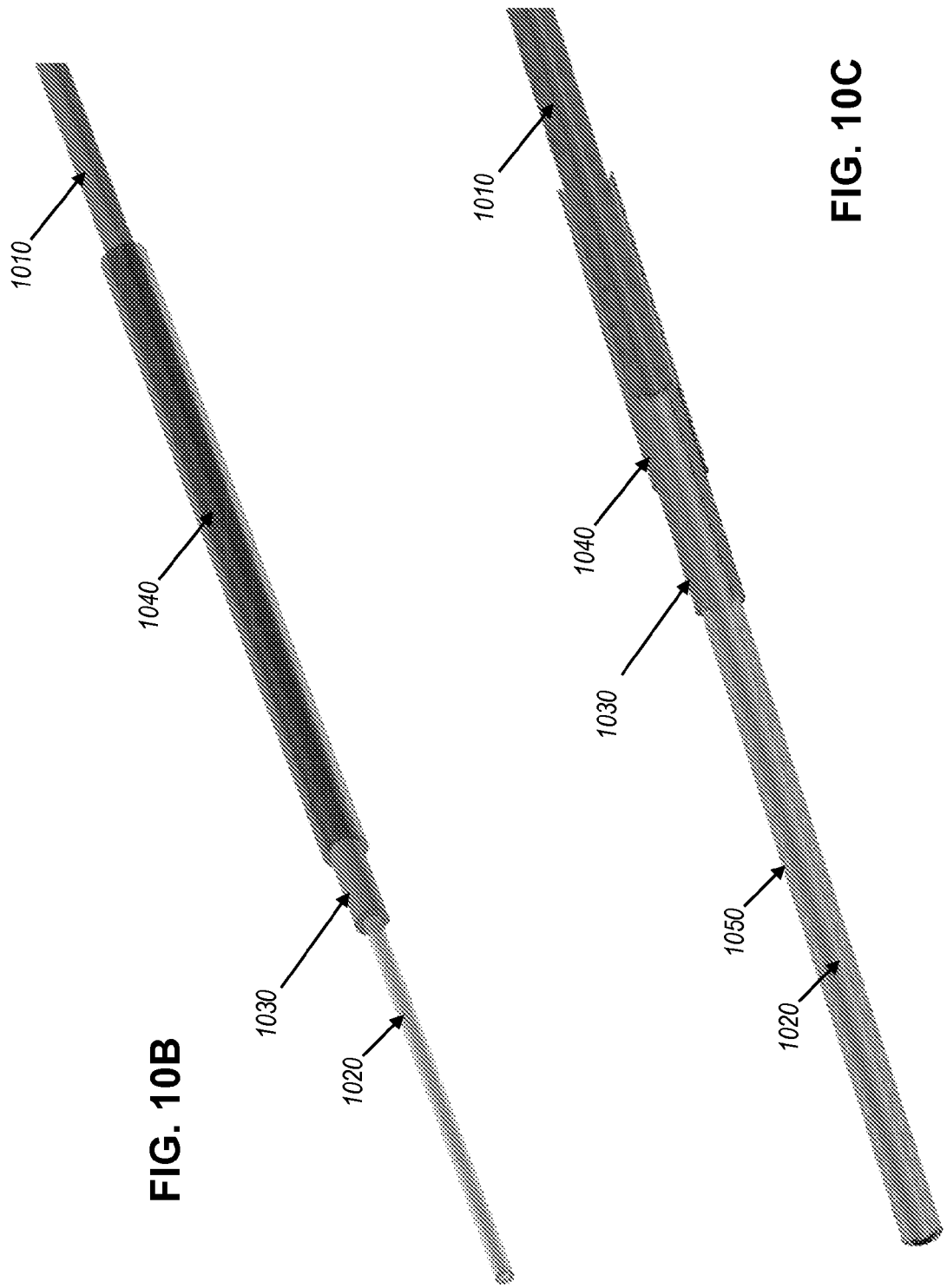

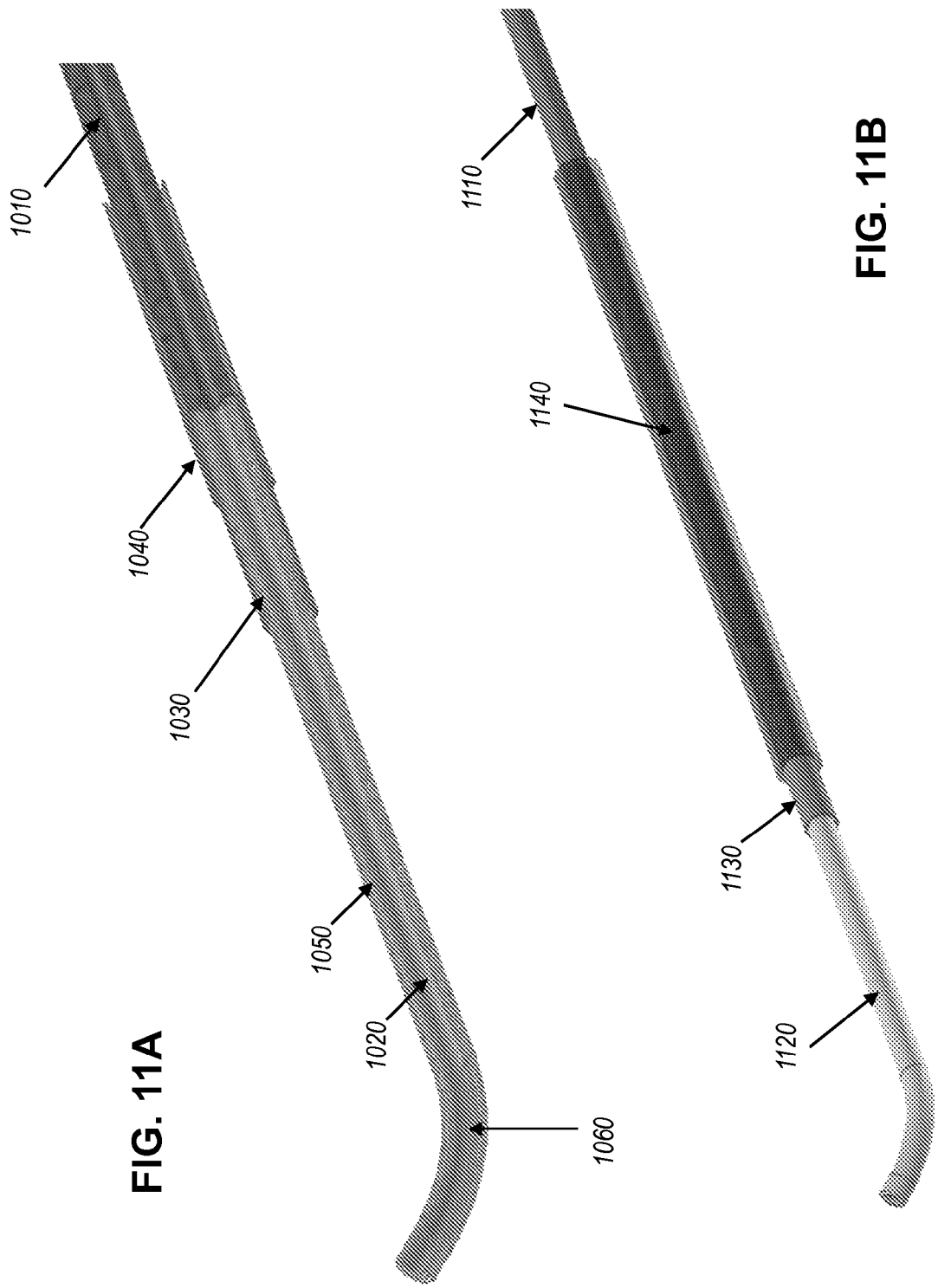

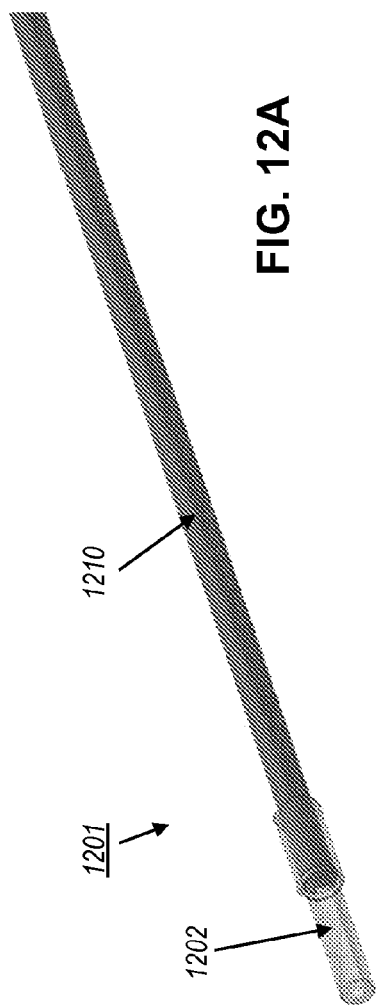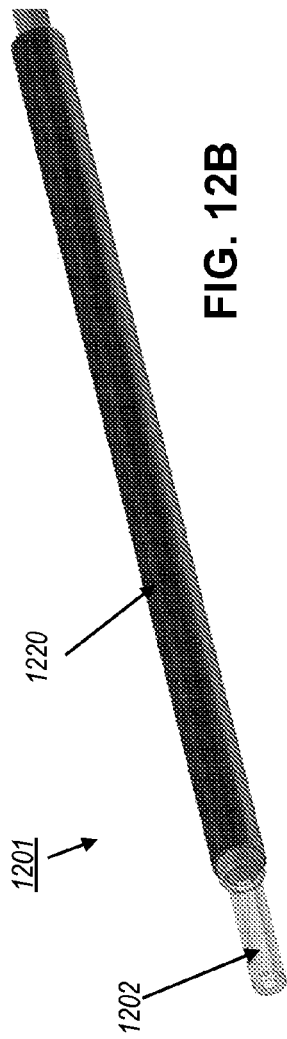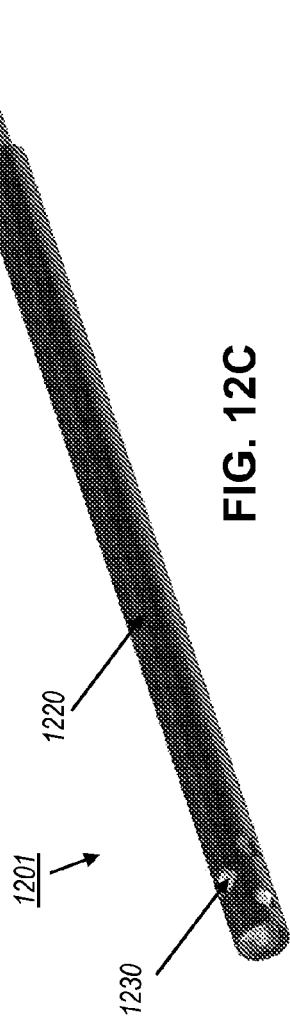

TWO-PART SURGICAL WAVEGUIDE

CROSS-REFERENCE TO RELATED APPLICATIONS

This application is a national phase filing under 35 U.S.C. §371 of international application number PCT/US2010/060109 entitled "TWO-PART SURGICAL WAVEGUIDE," filed on Dec. 13, 2010, which claims benefit of Provisional Patent Application No. 61/286,676 entitled "TWO-PART SURGICAL WAVEGUIDE," filed on Dec. 15, 2009, the entire contents of each of these prior applications is incorporated herein by reference.

TECHNICAL FIELD

This invention relates to waveguides for surgical applications.

BACKGROUND

Lasers are prevalent in many areas of medicine today. For example, lasers find application in diverse medical areas, such as surgery, veterinary medicine, dentistry, ophthalmology, and in aesthetic medical procedures.

In many of these applications, an optical fiber is used to deliver radiation from a laser to the target region of the patient. Conventional optical fibers are excellent waveguides for radiation having wavelengths in the visible or near-infrared portion of the electromagnetic spectrum (e.g., wavelengths of about 2 microns or less). However, conventional optical fibers are, in general, not suitable in applications where high power laser radiation with relatively long wavelengths is used. Accordingly, many medical laser systems that deliver high power (e.g., about 10 Watts or more), long wavelength (e.g., greater than about 2 microns), do so using an articulated arm that includes optical components that guide the laser radiation through rigid conduits or free space from the laser to the target.

SUMMARY

Two-part conduits are described for use in guiding light from a source (e.g., a laser) to a patient for surgical purposes. The conduits include a proximal portion, close to the source, and a distal portion closer to the patient. The conduit portions, while both being capable of guiding light from the source, are different in some way. For example, the proximal portion can be a flexible waveguide, while the distal portion can be a rigid waveguide.

Alternatively, or additionally, the distal portion can be thermally more robust than the proximal portion, so that any failure in the conduit due to heating occurs in the proximal portion, further away from the patient.

In some embodiments, the proximal portion is substantially longer than the distal portion (e.g., the proximal portion can be 90% or more of the length of the conduit), and can be formed from a less expensive type of waveguide (e.g., a waveguide that can be manufactured in longer lengths more readily) than the distal portion.

In certain embodiments, the distal portion can be selected to provide a different beam size or shape at the patient than could be provided by the waveguide used for the proximal portion.

In general, in one aspect, the invention features an apparatus that includes a light source configured to provide radiation at a wavelength $\lambda$ and a conduit configured to direct radiation at a wavelength $\lambda$ from the light source to a target location of a patient. The conduit includes a first optical waveguide extending along a waveguide axis, the first optical waveguide being a flexible waveguide having a hollow core, the first optical waveguide being configured to guide the radiation at $\lambda$ through the core along the waveguide axis; and a second optical waveguide extending along the waveguide axis, the second optical waveguide having a hollow core and being coupled to the first optical waveguide to receive the radiation from the first optical waveguide and to deliver the radiation to the target location. The first optical waveguide is a photonic crystal fiber and the second optical waveguide is not a photonic crystal fiber waveguide.

Embodiments of the apparatus can include one or more of the following features. For example, the first optical waveguide can be an OmniGuide BeamPath™ photonic crystal fiber. The photonic crystal fiber can include a dielectric confinement region surrounding the hollow core. The dielectric confinement region can include a layer of a first dielectric material arranged in a spiral around the waveguide axis. The first dielectric material can be a chalcogenide glass. The dielectric confinement region can include a second dielectric material arranged in a spiral around the waveguide axis. The second dielectric material is different from the first dielectric material. The first dielectric material can be an inorganic glass (e.g., a chalcogenide glass) and the second dielectric material is a polymer.

The first optical waveguide can be sufficiently flexible to guide the radiation to the target location while a portion of the first optical waveguide is bent through an angle of about 90 degrees or more and the portion has a radius of curvature of about 12 centimeters or less. The radiation can have an average power at the output end of about 1 Watt or more while the portion of the first optical waveguide is bent through an angle of about 90 degrees or more and the portion has a radius of curvature of about 12 centimeters or less. The radiation can have an average power at the output end of about 5 Watts or more while the portion of the first optical waveguide is bent through an angle of about 90 degrees or more and the portion has a radius of curvature of about 12 centimeters or less. The first optical waveguide can be sufficiently flexible to guide the radiation to the target location while the portion of the first optical waveguide is bent through an angle of about 90 degrees or more and the portion has a radius of curvature of about 10 centimeters or less. The first optical waveguide can be sufficiently flexible to guide the radiation to the target location while the portion of the first optical waveguide is bent through an angle of about 90 degrees or more and the portion has a radius of curvature of about 5 centimeters or less.

A length of the first optical waveguide can be 80% or more (e.g., 90% or more, 95% or more, 98% or more) of a length of the conduit. The first optical waveguide can be 1 m or more (e.g., 1.5 m or more, 2 m or more, 3 m or more, 5 m or more) in length. The first optical waveguide can be drawn from a preform.

The second optical waveguide can include a metal tube extending along the waveguide axis. The second optical waveguide can include one or more dielectric layers extending along the waveguide axis between the metal tube and the hollow core. The second optical waveguide can be formed from a ceramic material. The ceramic material can be $Al_2O_3$. The second optical waveguide can include a layer of a metal adjacent the core. The metal can be silver or gold. A length of the second optical waveguide can be 10% or less (e.g., 8% or less, 5% or less, 3% or less, 2% or less) of a length of the conduit. The second optical waveguide can have a length of 30 cm or less (e.g., 25 cm or less, 20 cm or less, 15 cm or less, 12 cm or less, 10 cm or less, 8 cm or less, 5 cm or less, 3 cm or less, 2 cm or less, 1 cm or less).

The waveguide axis can be entirely straight along the length of the second optical waveguide. The waveguide axis can include a bent portion along the length of the second optical waveguide.

The second optical waveguide can be a rigid waveguide or a flexible waveguide. In some embodiments, the second optical waveguide is more flexible than the first optical waveguide.

The hollow core of the first optical waveguide can have a diameter that is the same as a diameter of the hollow core of the second optical axis at an interface between the first and second optical waveguides. A diameter of the hollow core of the second optical waveguide can be constant along its length. Alternatively, the diameter of the hollow core of the second optical waveguide can vary along its length. In some embodiments, the diameter of the hollow core of the second optical waveguide increases along its length from an interface between the first and second optical waveguides to the output end of the conduit. In certain embodiments, the diameter of the hollow core of the second optical waveguide decreases along its length from an interface between the first and second optical waveguides to the output end of the conduit.

The second optical waveguide can be formed from a material that has a melting point of 500° C. or more (e.g., 1,000° C. or more, 2,000° C. or more).

The first and second optical waveguides can have different outer diameters. The outer diameter of the first optical waveguide can be larger than the outer diameter of the second optical waveguide.

The light source can be a laser light source. The laser light source can be a $CO_2$ laser or a YAG laser (e.g., Nd:YAG laser or Er:YAG laser). $\lambda$ is about 2,000 μm or more. In some embodiments, 10.6 μm.

The apparatus can include a handpiece attached to the first and/or second optical waveguides, wherein the handpiece allows an operator to control the orientation of the output end of the conduit to direct the radiation to the target location of the patient.

In general, in another aspect, the invention features an apparatus that includes a light source configured to provide radiation at a wavelength $\lambda$ and a conduit configured to direct radiation at a wavelength $\lambda$ from the light source to a target location of a patient. The conduit includes a first optical waveguide extending along a waveguide axis, the first optical waveguide being a flexible waveguide having a hollow core, the first optical waveguide being configured to guide the radiation at $\lambda$ through the core along the waveguide axis; and a second optical waveguide extending along the waveguide axis, the second optical waveguide having a hollow core and being coupled to the first optical waveguide to receive the radiation from the first optical waveguide and to deliver the radiation to the target location. The first and second optical waveguides have different thermal properties (e.g., have different temperatures at which they fail to guide the radiation at $\lambda$). Embodiments of the apparatus can include one or more of the features of other aspects.

In general, in another aspect, the invention features an apparatus that includes a light source configured to provide radiation at a wavelength $\lambda$ and a conduit configured to direct radiation at a wavelength $\lambda$ from the light source to a target location of a patient. The conduit includes a first optical waveguide extending along a waveguide axis, the first optical waveguide being a flexible waveguide having a hollow core, the first optical waveguide being configured to guide the radiation at $\lambda$ through the core along the waveguide axis; and a second optical waveguide extending along the waveguide axis, the second optical waveguide having a hollow core and being coupled to the first optical waveguide to receive the radiation from the first optical waveguide and to deliver the radiation to the target location. The first and second optical waveguides have different mechanical properties (e.g., the first optical waveguide can be more or less flexible than the second optical waveguide). Embodiments of the apparatus can include one or more of the features of other aspects.

In general, in another aspect, the invention features an apparatus that includes a light source configured to provide radiation at a wavelength $\lambda$ and a conduit configured to direct radiation at a wavelength $\lambda$ from the light source to a target location of a patient. The conduit includes a first optical waveguide extending along a waveguide axis, the first optical waveguide being a flexible waveguide having a hollow core, the first optical waveguide being configured to guide the radiation at $\lambda$ through the core along the waveguide axis; and a second optical waveguide extending along the waveguide axis, the second optical waveguide having a hollow core and being coupled to the first optical waveguide to receive the radiation from the first optical waveguide and to deliver the radiation to the target location. The first optical waveguide is a photonic crystal fiber and the second optical waveguide is a ceramic waveguide. Embodiments of the apparatus can include one or more of the features of other aspects.

In general, in another aspect, the invention features an apparatus that includes a light source configured to provide radiation at a wavelength $\lambda$ and a conduit configured to direct radiation at a wavelength $\lambda$ from the light source to a target location of a patient. The conduit includes a first optical waveguide extending along a waveguide axis, the first optical waveguide being a flexible waveguide having a hollow core, the first optical waveguide being configured to guide the radiation at $\lambda$ through the core along the waveguide axis; and a second optical waveguide extending along the waveguide axis, the second optical waveguide having a hollow core and being coupled to the first optical waveguide to receive the radiation from the first optical waveguide and to deliver the radiation to the target location. The first optical waveguide is a photonic crystal fiber and the second optical waveguide comprises a metal tube. Embodiments of the apparatus can include one or more of the features of other aspects.

In general, in another aspect, the invention features an apparatus that includes a light source configured to provide radiation at a wavelength $\lambda$ and a conduit configured to direct radiation at a wavelength $\lambda$ from the light source to a target location of a patient. The conduit includes a first optical waveguide extending along a waveguide axis, the first optical waveguide being a flexible waveguide having a hollow core, the first optical waveguide being configured to guide the radiation at $\lambda$ through the core along the waveguide axis; and a second optical waveguide extending along the waveguide axis, the second optical waveguide having a hollow core and being coupled to the first optical waveguide to receive the radiation from the first optical waveguide and to deliver the radiation to the target location. The first and second optical waveguides are photonic crystal fibers having different core diameters and/or different outer diameters. Embodiments of the apparatus can include one or more of the features of other aspects.

The details of one or more embodiments of the invention are set forth in the accompanying drawings and the description below. Other features and advantages will be apparent from the description and drawings, and from the claims.

DESCRIPTION OF DRAWINGS

FIG. 1A is a schematic diagram of an embodiment of a laser medical system that includes a two-part conduit.

FIG. 1B is a schematic diagram of the two-part conduit.

FIGS. 3A and 3B are exemplary embodiments of two-part conduits.

FIGS. 4A and 4B are exemplary embodiments of two-part conduits.

FIGS. 5A and 5B are exemplary embodiments of two-part conduits.

FIGS. 6A and 6B are exemplary embodiments of two-part conduits.

FIGS. 7A and 7B are exemplary embodiments of two-part conduits.

FIGS. 10A-10C are exemplary embodiments of two-part conduits.

FIGS. 11A and 11B are exemplary embodiments of two-part conduits.

FIGS. 12A-12C are exemplary embodiments of two-part conduits.

Like reference symbols in the various drawings indicate like elements.

DETAILED DESCRIPTION

Figure 2A:
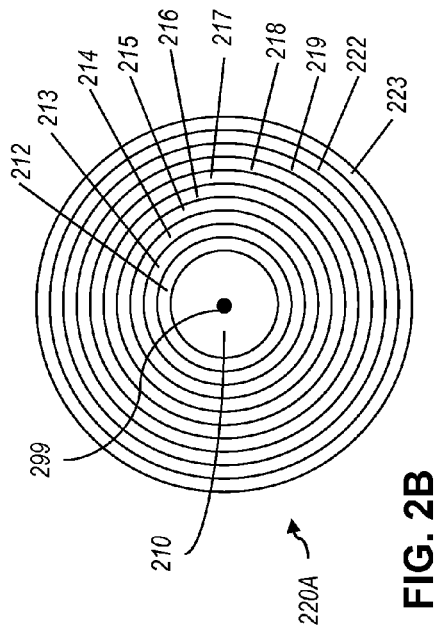
FIG. 2A is a cross-section view of an embodiment of a photonic crystal fiber.

Referring to FIG. 1A, a medical laser system 100 includes a $CO_2$ laser 110, and a two-part waveguide conduit 120 having a hollow core to guide radiation 112 from the laser to a target location 99 of a patient. Radiation 112 has a wavelength of 10.6 microns. Laser radiation 112 is coupled by a coupling assembly 130 into the hollow core of conduit 120, which delivers the radiation through a handpiece 140 to target location 99. During use, an operator (e.g., a medical practitioner, such as a surgeon, a dentist, an ophthalmologist, or a veterinarian) grips a portion 142 of handpiece 140, and manipulates the handpiece to direct laser radiation 113 emitted from an output end of conduit 120 to target location 99 in order to perform a therapeutic function at the target location. For example, the radiation can be used to excise, incise, ablate, or vaporize tissue at the target location.

$CO_2$ laser 110 is controlled by an electronic controller 150 for setting and displaying operating parameters of the system. The operator controls delivery of the laser radiation using a remote control 152, such as a foot pedal. In some embodiments, the remote control is a component of handpiece 140, allowing the operator to control the direction of emitted laser radiation and delivery of the laser radiation with one hand or both hands.

In addition to grip portion 142, handpiece 140 includes a stand off tip 144, which maintains a desired distance (e.g., from about 0.1 millimeters to about 30 millimeters) between the output end of conduit 120 and target tissue 99. The stand off tip assists the operator in positioning the output end of conduit 120 relative to target location 99, and can also reduce clogging of the output end due to debris at the target location. In some embodiments, handpiece 140 includes optical components (e.g., a lens or lenses), which focus the beam emitted from the fiber to a desired spot size. The waist of the focused beam can be located at or near the distal end of the stand off tip.

In some embodiments, conduit 120 can be easily installed and removed from coupling assembly 130, and from handpiece 140 (e.g., using conventional fiber optic connectors). This can facilitate ease of use of the system in single-use applications, where the fiber is replaced after each procedure.

Typically, $CO_2$ laser 110 has an average output power of about 5 Watts to about 80 Watts at 10.6 microns (e.g., about 10 Watts or more, about 20 Watts or more). In many applications, laser powers of about 5 Watts to about 30 Watts are sufficient for the system to perform its intended function. For example, where system 100 is being used to excise or incise tissue, the radiation is confined to a small spot size and a laser having an average output power in this range is sufficient.

In certain embodiments, however, laser 110 can have an output power as high as about 100 Watts or more (e.g., up to about 500 Watts). For example, in applications where system 100 is used to vaporize tissue over a relatively large area (e.g., several square millimeters or centimeters), extremely high power lasers may be desirable.

Conduit 120 can deliver the radiation from laser 110 to the target location with relatively high efficiency. For example, the fiber average output power can be about 50% or more of the fiber input energy (e.g., about 60% or more, about 70% or more, about 80% or more). Accordingly, the conduit's output power can be about 3 Watts or more (e.g., about 8 Watts or more, about 10 Watts or more, about 15 Watts or more). In certain embodiments, however, the average output power from the conduit can be less than 50% of the laser power, and still be sufficiently high to perform the intended procedure. For example, in some embodiments, the conduit average output power can be from about 20% to about 50% of the laser average output power.

The length of conduit 120 can vary as desired. In some embodiments, the conduit is about 1.2 meters long or more (e.g., about 1.5 meters or more, about 2 meters or more, about 3 meters or more, about 5 meters or more). The length is typically dependent on the specific application for which the laser system is used. In applications where laser 110 can be positioned close to the patient, and/or where the range of motion of the handpiece desired for the application is relatively small, the length of the conduit can be relatively short (e.g., about 1.5 meters or less, about 1.2 meters or less, about 1 meter or less). In certain applications, the length of conduit 120 can be very short (e.g., about 50 centimeters or less, about 20 centimeters or less, about 10 centimeters or less). For example, very short lengths of conduit may be useful in procedures where the system can deliver radiation from the laser to the fiber by some other means (e.g., a different waveguide or an articulated arm). Very short conduit lengths may be useful for nose and ear procedures, for example.

However, in applications where it is inconvenient for the laser to be placed in close proximity to the patient and/or where a large range of motion of the handpiece is desired, the length of the conduit is longer (e.g., about 2 meters or more, about 5 meters or more, about 8 meters or more). For example, in surgical applications, where a large team of medical practitioners is needed in close proximity to the patient, it may be desirable to place the laser away from the operating table (e.g., in the corner of the operating room, or in a different room entirely). In such situations, a longer conduit may be desirable.

In general, at least a portion of conduit 120 (e.g., a proximal portion, as discussed below) is flexible, and can be bent to relatively small radii of curvature over relatively large angles without significantly impacting its performance (e.g., without causing the conduit to fail, or without reducing the conduit transmission to a level where the system cannot be used for its intended use while the fiber is bent). In some embodiments, an operator can bend conduit 120 to have a relatively small radius of curvature, such as about 15 cm or less (e.g., about 10 cm or less, about 8 cm or less, about 5 cm or less, about 3 cm or less) while still delivering sufficient power to the target location for the system to perform its function.

In general, the angle through which conduit 120 is bent can vary, and usually depends on the procedure being performed. For example, in some embodiments, the conduit can be bent through about 90° or more (e.g., about 120° or more, about 150° or more).

Losses of transmitted power due to the operator bending conduit 120 may be relatively small. In general, losses due to bends should not significantly damage the conduit, e.g., causing it to fail, or reduce the conduit output power to a level where the system can no longer perform the function for which it is designed. Embodiments of conduit 120 (e.g., about 1 meter or more in length) can be bent through 90° with a bend radius of about 5 centimeters or less, and still transmit about 30% or more (e.g., about 50% or more, about 70% or more) of radiation coupled into the conduit at the guided wavelength. These conduits can provide such transmission characteristics and provide average output power of about 3 Watts or more (e.g., about 5 Watts or more, about 8 Watts or more, about 10 Watts or more).

The quality of the beam of the laser radiation emitted from the output end of conduit 120 can be relatively good. For example, the beam can have a low $M^2$ value, such as about 4 or less (e.g., about 3 or less, about 2.5 or less, about 2 or less). $M^2$ is a parameter commonly used to describe laser beam quality, where an $M^2$ value of about 1 corresponds to a $TEM_{00}$ beam emitted from a laser, which has a perfect Gaussian profile. The $M^2$ value is related to the minimum spot size that can be formed from the beam according to the formula:

$$d_s=1.27 f \lambda M^2/d_b \quad (1)$$

where $d_s$ is the minimum spot diameter, $d_b$ is the beam diameter prior to being focused to the spot by a lens having focal length f. Accordingly, the minimum possible spot size a beam can be focused is proportional to the $M^2$ value for the beam. Practically, beams having smaller values of $M^2$ can provide higher radiation power densities to the target area, with less damage to surrounding tissue due to the decreased spot size.

The spot size of radiation delivered by conduit 120 to the target tissue can be relatively small. For example, in certain embodiments, the spot can have a diameter of about 500 microns or less (e.g., about 300 microns or less, about 200 microns or less, such as about 100 microns) at a desired working distance from the conduit's output end (e.g., from about 0.1 mm to about 3 mm). A small spot size may be desirable where system 100 is being used to excise or incise tissue or in other applications where substantial precision in the delivery of the radiation is desired. Alternatively, in applications where tissue is to be ablated or vaporized, and/or a lesser level of precision is sufficient, the spot size can be relatively large (e.g., having a diameter of about 2 millimeters or more, about 3 millimeters or more, about 4 millimeters or more).

While laser 110 is a $CO_2$ laser, conduits can be used in medical laser systems that use other types or lasers, operating at wavelengths different from 10.6 microns. In general, medical laser systems can provide radiation at ultraviolet (UV), visible, or infrared (IR) wavelengths. Lasers delivering IR radiation, for example, emit radiation having a wavelength between about 0.7 microns and about 20 microns (e.g., between about 2 to about 5 microns or between about 8 to about 12 microns). Conduits having hollow cores, such as hollow core photonic crystal fibers, are well-suited for use with laser systems having wavelengths of about 2 microns or more, since gases that commonly occupy the core have relatively low absorptions at these wavelengths compared to many dielectric materials (e.g., silica-based glasses and various polymers). In addition to $CO_2$ lasers, other examples of lasers which can emit IR radiation include Nd:YAG lasers (e.g., at 1.064 microns), Er:YAG lasers (e.g., at 2.94 microns), Er, Cr:YSGG (Erbium, Chromium doped Yttrium Scandium Gallium Garnet) lasers (e.g., at 2.796 microns), Ho:YAG lasers (e.g., at 2.1 microns), free electron lasers (e.g., in the 6 to 7 micron range), and quantum cascade lasers (e.g., in the 3 to 5 micron range).

In general, the type of laser used in a medical laser system depends on the purpose for which the system is designed. The type of laser can be selected depending on whether the system is to be used in surgical procedures, in diagnosis, or in physiologic studies. For example, an argon laser, which delivers in the blue and green regions of the visible light spectrum, with two energy peaks, at 488 nm and 514 nm, can be used for photocoagulation. A dye laser, which is a laser with organic dye dissolved in a solvent as the active medium whose beam is in the visible light spectrum, can be used in photodynamic therapy. Excimer lasers provide radiation in the ultraviolet spectrum, penetrates tissues only a small distance, can be used to break chemical bonds of molecules in tissue instead of generating heat to destroy tissue. Such lasers can be used in ophthalmological procedures and laser angioplasty. Ho:YAG lasers can provide radiation in the near infrared spectrum and can be used for photocoagulation and photoablation. Krypton lasers provide radiation in the yellow-red visible light spectrum, and can be used for photocoagulation. Radiation from KTP lasers can be frequency-doubled to provide radiation in the green visible light spectrum and can be used for photoablation and photocoagulation. Nd:YAG lasers can be for photocoagulation and photoablation. Pulsed dye lasers can be used to provide in the yellow visible light spectrum (e.g., with a wavelength of 577 nm or 585 nm), with alternating on and off phases of a few microseconds each, and can be used to decolorize pigmented lesions.

In general, laser systems can use continuous wave or pulsed lasers. Furthermore, while $CO_2$ lasers are typically used at average output powers of about 5 Watts to about 100 Watts, photonic crystal fibers can generally be used with a variety of laser powers. For example, average laser power can be in the milliWatt range in certain systems, up to as much as several hundred Watts (e.g., about 200 Watts or more) in extremely high power systems.

For high power systems, the average power density guided by conduit 120 can be extremely high. For example, power density in the conduit, or exiting the conduit's core) can be about $10^3$ W/cm$^2$ or more (e.g., about $10^4$ W/cm$^2$ or more, about $10^5$ W/cm$^2$ or more, $10^6$ W/cm$^2$ or more).

Referring to FIG. 1B, two-part conduit 120 includes a proximal portion 121 and a distal portion 122 (also referred to as the tip). Proximal portion 121 receives light from the laser and guides it to distal portion 122. The proximal and distal portions are configured so that light guided by proximal portion 121 is coupled into the core of distal portion 122, which then guides the light to the target. In addition to proximal portion 121 and distal portion 122, conduit 120 can include one or more interface elements 140 for attaching distal portion 122 to proximal portion 121, also referred to as junction elements.

In general, proximal portion 121 and distal portion 122 have different properties, being configured to fulfill different functions in addition to guiding light from the laser to the target. For example, proximal portion 121 can be a flexible waveguide that is relatively long (e.g., about one meter or more, about 1.5 meters or more, about 2 meters or more, about 3 meters or more), designed to reliably deliver radiation reliably from the laser to close to the patient, while distal portion 122 is comparably shorter (e.g., about 20 cm or less, about 15 cm or less, about 10 cm or less, about 5 cm or less, about 2 cm or less) and is tailored for delivering the radiation to the target tissue.

In some embodiments, the proximal and distal portions can have different thermal properties. For example, distal portion 122 can be thermally more robust than proximal portion 121. In other words, distal portion 122 can be formed from material(s) that have higher melting temperatures than the material(s) from which proximal portion 121 is formed. In such cases, proximal portion 121 can act as a thermal fuse, which fails before distal portion 122 in the event that the conduit overheats. This may be beneficial as failure can occur away from the patient, limiting unwanted exposure of the light to the patient. Exemplary embodiments include using a photonic crystal fiber formed from a polymer (with or without an inorganic glass) as the proximal portion and a ceramic or metallic waveguide as the distal portion.

In certain embodiments, the proximal and distal portions can have different output beam diameters. For example, proximal portion 121 can be have a core diameter that is relatively large compared to distal portion 122, the proximal portion being configured to provide reliable transmission properties (which provide an output beam of a certain diameter), while distal portion 122 is configured to provide an output beam diameter sized for a specific surgical procedure. For example, the dimensions (e.g., core diameter) of distal portion 122 can be selected to provide a smallest spot size (measured, e.g., as the cross-sectional dimension of the beam at its waist that is 10% of its peak intensity at its waist) that is about 75% or less (e.g., about 50% or less, about 40% or less, about 30% or less, about 20% or less) than the smallest spot size of an output beam of the waveguide used for the proximal portion.

In some embodiments, distal portion 122 can be configured to provide a beam spot diameter of about 1,000 µm or less (e.g., about 500 µm or less, about 300 µm or less, about 200 µm or less, about 100 µm or less). For example, a photonic crystal fiber (e.g., having a length of about 5 mm or more) have a core diameter of about 315 µm can be used to provide a beam spot of diameter about 205 µm for light having a wavelength 10.6 µm. A beam spot diameter of about 500 µm (1,000 µm) may be achieved using, e.g., a photonic crystal fiber with a core diameter of about 750-800 µm (1,400-1,600 µm) for light having a wavelength 10.6 µm Distal portion 122 can be more rigid than proximal portion 121. For example, proximal portion 121 can be a flexible waveguide, such as a photonic crystal fiber, while distal portion is a rigid waveguide (e.g., a ceramic or metal waveguide). Rigid waveguides can be used in applications where precise control of the position and orientation of the output end is desired, so flexibility of the conduit at this position is undesirable. Alternatively, in certain embodiments, distal portion 122 can be more flexible that proximal portion 121.

In some embodiments, conduit 120 includes a jacket which can provide additional mechanical strength and provide an additional junction between distal portion 122 and proximal portion 121, or can serve entirely as a junction element without additional parts. A jacket, for example, can increase laser safety and reliability of the device. Different jacket designs can be used to control mechanical properties of the device over its length, e.g., to provide desired flexibility characteristics. Various distal portion designs can be implemented to achieve desired mechanical, dimensional and optical characteristics and address reliability at the distal end of the device. Examples of two-part conduits are described below.

In certain embodiments, distal portion 122 can be less rigid than proximal portion 121. For example, distal portion 122 can be bendable to smaller radius than proximal portion 121, not only mechanically but also having higher power capacity for smaller bends than the proximal portion, thus allowing the distal portion to bend more without a substantial decrease in output power. For example, in some embodiments, a 10 cm long distal portion 122 can be bent through 90° with a bend radius of about 3 centimeters or less (e.g., about 2 cm or less, about 1 cm or less), and still transmit about 30% or more (e.g., about 50% or more, about 70% or more, about 80% or more, about 90% or more) of radiation coupled into the conduit at the guided wavelength. These conduits can provide such transmission characteristics and provide average output power of about 3 Watts or more (e.g., about 5 Watts or more, about 8 Watts or more, about 10 Watts or more).

In general, at least one of proximal portion 121 and distal portion 122 is a photonic crystal fiber. Embodiments, of photonic crystal fibers are described below.

In some embodiments, both portions 121 and 122 are photonic crystal fibers. The photonic crystal fibers can have different structures. For example the different photonic crystals can have different core diameters. Such configurations can be used, for example, where specific beam diameters are desired at the target. For example, the beam diameter scales roughly in proportion to the core diameter, so in applications where a small beam diameter is used, the distal photonic crystal fiber can have a smaller core diameter than the proximal portion.

In some embodiments, the distal photonic crystal fiber can be tapered, having a core diameter that matches the core diameter of the proximal photonic crystal fiber where the two fibers interface, but the core size changing (e.g., increasing or decreasing) the closer it gets to the output end of the conduit. The core of the tip can be tapered to provide a reduced beam spot size and/or to increase beam divergence at the output end.

In some embodiments, the two different photonic crystal fibers have different outer diameters. For example, distal portion 122 can have a narrower outer diameter than proximal portion 121, e.g., to allow the distal portion to be threaded through narrow channels (e.g., into the patient's ear canal or nasal canal), while proximal portion 121 has a thicker outer diameter so that the majority of the two-part conduit is flexible and robust.

In some embodiments, either proximal portion 121 or distal portion 122 is a not a photonic crystal fiber waveguide, but a different type of waveguide (e.g., a ceramic waveguide, a hollow metal tube).

In general, both proximal portion 121 and distal portion 122 are waveguides for the wavelength of light used for the surgical procedure. In other words, both the proximal and distal portions both substantially confine at least some modes of the light to a core and guide the light along an axis (e.g., a straight or curved axis) along which the core extends. Distal portion 122 may be more lossy or less lossy per unit of length compared to proximal portion 121. In some embodiments, distal portion 122 can be a lossy, leaky-mode waveguide.

Prior to discussing specific examples of two-part conduits, photonic crystal fibers are described. Referring to FIG. 2A, in general, photonic crystal fiber 120 includes a core 210, which is surrounded by a confinement region 220 extending along a waveguide axis 299 (normal to the plane of FIG. 2A). Confinement region 220 is surrounded by a cladding 230 (e.g., a polymer cladding), which provides mechanical support and protects the core and confinement region from environmental hazards. Confinement region 220 includes a photonic crystal structure that substantially confines radiation at a wavelength $\lambda$ to core 210. Examples of such structures are described with reference to FIGS. 2B-2D below. As used herein, a photonic crystal is a structure (e.g., a dielectric structure) with a refractive index modulation (e.g., a periodic refractive index modulation) that produces a photonic bandgap in the photonic crystal. An example of such a structure, giving rise to a one dimensional refractive index modulation, is a stack of dielectric layers of high and low refractive index, where the layers have substantially the same optical thickness. A photonic bandgap, as used herein, is a range of frequencies in which there are no accessible extended (i.e., propagating, non-localized) states in the dielectric structure. Typically the structure is a periodic dielectric structure, but it may also include, e.g., more complex "quasi-crystals." The bandgap can be used to confine, guide, and/or localize light by combining the photonic crystal with "defect" regions that deviate from the bandgap structure. Moreover, there are accessible extended states for frequencies both below and above the gap, allowing light to be confined even in lower-index regions (in contrast to index-guided TIR structures). The term "accessible" states means those states with which coupling is not already forbidden by some symmetry or conservation law of the system. For example, in two-dimensional systems, polarization is conserved, so only states of a similar polarization need to be excluded from the bandgap. In a waveguide with uniform cross-section (such as a typical fiber), the wavevector $\beta$ is conserved, so only states with a given $\beta$ need to be excluded from the bandgap to support photonic crystal guided modes. Moreover, in a waveguide with cylindrical symmetry, the "angular momentum" index m is conserved, so only modes with the same m need to be excluded from the bandgap. In short, for high-symmetry systems the requirements for photonic bandgaps are considerably relaxed compared to "complete" bandgaps in which all states, regardless of symmetry, are excluded.

Theoretically, a photonic crystal is only completely reflective in the bandgap when the index modulation in the photonic crystal has an infinite extent. Otherwise, incident radiation can "tunnel" through the photonic crystal via an evanescent mode that couples propagating modes on either side of the photonic crystal. In practice, however, the rate of such tunneling decreases exponentially with photonic crystal thickness (e.g., the number of alternating layers). It also decreases with the magnitude of the index contrast in the confinement region.

Furthermore, a photonic bandgap may extend over only a relatively small region of propagation vectors. For example, a dielectric stack may be highly reflective for a normally incident ray and yet only partially reflective for an obliquely incident ray. A "complete photonic bandgap" is a bandgap that extends over all possible wavevectors and all polarizations. Generally, a complete photonic bandgap is only associated with a photonic crystal having index modulations along three dimensions. However, in the context of EM radiation incident on a photonic crystal from an adjacent dielectric material, we can also define an "omnidirectional photonic bandgap," which is a photonic bandgap for all possible wavevectors and polarizations for which the adjacent dielectric material supports propagating EM modes. Equivalently, an omnidirectional photonic bandgap can be defined as a photonic band gap for all EM modes above the light line, wherein the light line defines the lowest frequency propagating mode supported by the material adjacent the photonic crystal. For example, in air the light line is approximately given by $\omega=c\beta$, where $\omega$ is the angular frequency of the radiation, $\beta$ is the wavevector, and c is the speed of light. A description of an omnidirectional planar reflector is disclosed in U.S. Pat. No. 6,130,780, the entire contents of which are incorporated herein by reference. Furthermore, the use of alternating dielectric layers to provide omnidirectional reflection (in a planar limit) for a cylindrical waveguide geometry is disclosed in Published PCT application WO 00/22466, the contents of which are incorporated herein by reference.

When confinement region 220 gives rise to an omnidirectional bandgap with respect to core 210, the guided modes are strongly confined because, in principle, any EM radiation incident on the confinement region from the core is completely reflected. As described above, however, such complete reflection only occurs when there are an infinite number of layers. For a finite number of layers (e.g., about 20 layers), an omnidirectional photonic bandgap may correspond to a reflectivity in a planar geometry of at least 95% for all angles of incidence ranging from 0° to 80° and for all polarizations of EM radiation having frequency in the omnidirectional bandgap. Furthermore, even when fiber 120 has a confinement region with a bandgap that is not omnidirectional, it may still support a strongly guided mode, e.g., a mode with radiation losses of less than 0.1 dB/km for a range of frequencies in the bandgap. Generally, whether or not the bandgap is omnidirectional will depend on the size of the bandgap produced by the alternating layer (which generally scales with index contrast of the two layers) and the lowest-index constituent of the photonic crystal.

Regarding the structure of photonic crystal fiber 120, in general, the diameter of core 210 (indicated by reference numeral 211 in FIG. 2A) can vary depending on the end-use application of system 100. For example, where a large spot size is desired, the core can be relatively large (e.g., about 1 mm or more, about 2 mm or more). Alternatively, when a small spot size is desired, core diameter 211 can be much smaller (e.g., about 500 microns or less, about 300 microns or less, about 200 microns or less, about 100 microns or less).

More generally, where fiber 120 is used in systems with other types of laser, and/or used to guide wavelengths other than 10.6 microns, the core diameter depends on the wavelength or wavelength range of the energy to be guided by the fiber, and on whether the fiber is a single or multimode fiber. For example, where the fiber is a single mode fiber for guiding visible wavelengths (e.g., between about 400 nm and about 800 nm) the core radius can be in the sub-micron to several micron range (e.g., from about 0.5 microns to about 5 microns). However, the core radius can be in the tens to thousands of microns range (e.g., from about 10 microns to about 2,000 microns, such as about 500 microns to about 1,000 microns), for example, where the fiber is a multimode fiber for guiding IR wavelengths. The core radius can be about 5$\lambda$ or more (e.g., about 10$\lambda$ or more, about 20$\lambda$ or more, about 50$\lambda$ or more, about 100$\lambda$ or more), where $\lambda$ is the wavelength of the guided energy.

An advantage of photonic crystal fibers is that fibers having small core diameters can be readily produced since fibers can be drawn from a perform, preserving the relative proportions of the fiber's cross-sectional structure while reducing the dimensions of that structure to small sizes in a controlled manner.

In photonic crystal fiber 120, core 220 is hollow. Alternatively, in embodiments where there are no fluids pumped through the core, core 220 can include any material or combination of materials that are rheologically compatible with the materials forming confinement region 220 and that have sufficiently high transmission properties at the guided wavelength(s). In some embodiments, core 220 includes a dielectric material (e.g., an amorphous dielectric material), such as an inorganic glass or a polymer. In certain embodiments, core 220 can include one or more dopant materials, such as those described in U.S. patent application Ser. No. 10/121,452, entitled "HIGH INDEX-CONTRAST FIBER WAVEGUIDES AND APPLICATIONS," filed Apr. 12, 2002 and now published under Pub. No. US-2003-0044158-A1, the entire contents of which are hereby incorporated by reference.

Cladding 230 can be formed from a polymer (e.g., an acrylate polymer, an olefin, a sulfone or a silicone polymer) or other material. Cladding 230 can be formed from a material that is also used to as part of confinement region 220, which are described below. In applications where the cladding comes in contact with a patient, it can be formed from materials that conform to FDA standards for medical devices. In these instances, silicone polymers, for example, may be particularly suited for use as the cladding material. Typically, cladding 230 protects the fiber from external damage. By selecting the appropriate thickness, composition, and/or structure, cladding 230 can also be designed to limit the flexibility of the fiber, e.g., to prevent damage by small radius of curvature bends.

In general, the thickness of fiber 120 can vary. The thickness is indicated by outer diameter (OD) 231 in FIG. 2A. OD 231 can be selected so that fiber 120 is compatible with other pieces of equipment. For example, fiber 120 can be made so that OD 231 is sufficiently small so that the fiber can be threaded through a channel in an endoscope or other tool (e.g., OD 231 can be about 2,000 microns or less). In some embodiments, fiber 120 has a relatively small OD (e.g., about 1,000 microns or less). Narrow fibers can be useful in applications where they are to be inserted into narrow spaces, such as through a patient's ear or urethra. Alternatively, in some embodiments, diameter 231 can be relatively large compared (e.g., about 3,000 microns or more). Large OD's can reduce the mechanical flexibility of the fiber, which can prevent the fiber from bending to small radii of curvature that damage the fiber or reduce its transmission to a level where the system can no longer perform its intended function.

In addition to cladding 230, fiber 200 may include additional components to limit bend radii. For example, the fiber may include a spirally wound material around its outer diameter (e.g., a spirally wound wire). Alternatively, or additionally, the fiber may include additional claddings to provide additional mechanical support.

Although the fiber can be bent (as discussed above), in some embodiments, the fiber may be constrained from bending to radii of curvature of less than about 20 cm (e.g., about 10 cm or less, 8 cm or less, 5 cm or less) during regular use in the application for which it is designed.

The cladding material may be selected so that the fiber is sterilizable. For example, the cladding material may be selected so that the fiber can withstand high temperatures (e.g., those experienced in an autoclave).

Figure 2B:
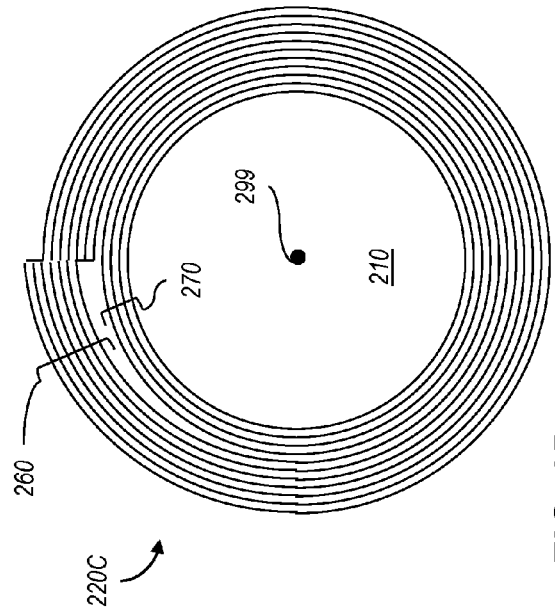
FIGS. 2B-2D are cross-sectional views of embodiments of confinement regions for photonic crystal fibers.

Turning to the structure and composition of confinement region 220, in some embodiments, photonic crystal fiber 120 is a Bragg fiber and confinement region 220 includes multiple alternating layers having high and low refractive indexes, where the high and low index layers have similar optical thickness. For example, referring to FIG. 2B, in some embodiments, confinement region 220A includes multiple annular dielectric layers of differing refractive index (i.e., layers composed of a high index material having a refractive index $n_H$, and layers composed of a low index material having a refractive index $n_L$), indicated as layers 212, 213, 214, 215, 216, 217, 218, 219, 222, and 223. Here, $n_H > n_L$, and $n_H - n_L$ can be, for example, about 0.01 or more, about 0.05 or more, about 0.1 or more, about 0.2 or more, about 0.5 or more. For convenience, only a few of the dielectric confinement layers are shown in FIG. 2B. In practice, confinement region 220A may include many more layers (e.g., about 15 layers or more, about 20 layers or more, about 30 layers or more, about 40 layers or more, about 50 layers or more, about 80 layers or more).

In some embodiments, confinement region 220 can give rise to an omnidirectional bandgap with respect to core 210, wherein the guided modes are strongly confined because, in principle, any EM radiation incident on the confinement region from the core is completely reflected. However, such complete reflection only occurs when there are an infinite number of layers. For a finite number of layers (e.g., about 20 layers), an omnidirectional photonic bandgap may correspond to a reflectivity in a planar geometry of at least 95% for all angles of incidence ranging from 0° to 80° and for all polarizations of EM radiation having frequency in the omnidirectional bandgap. Furthermore, even when fiber 120 has a confinement region with a bandgap that is not omnidirectional, it may still support a strongly guided mode, e.g., a mode with radiation losses of less than 0.1 dB/km for a range of frequencies in the bandgap. Generally, whether or not the bandgap is omnidirectional will depend on the size of the bandgap produced by the alternating layers (which generally scales with index contrast of the two layers) and the lowest-index constituent of the photonic crystal.

The existence of an omnidirectional bandgap, however, may not be necessary for useful application of fiber 120. For example, in some embodiments, a laser beam used to establish the propagating field in the fiber is a $TEM_{00}$ mode. This mode can couple with high efficiency to the $HE_{11}$ mode of a suitably designed fiber. Thus, for successful application of the fiber for transmission of laser energy, it may only be necessary that the loss of this one mode be sufficiently low. More generally, it may be sufficient that the fiber support only a number of low loss modes (e.g., the $HE_{11}$ mode and the modes that couple to it from simple perturbations, such as bending of the fiber). In other words, photonic bandgap fibers may be designed to minimize the losses of one or a group of modes in the fiber, without necessarily possessing an omnidirectional bandgap.

For a planar dielectric reflector, it is well-known that, for normal incidence, a maximum band gap is obtained for a "quarter-wave" stack in which each layer has equal optical thickness $\lambda/4$, or equivalently $n_{hi} d_{hi} = n_{lo} d_{lo} = \lambda/4$, where $d_{hi/lo}$ and $n_{hi/lo}$ refer to the thickness and refractive index, respectively, of high-index and low-index layers in the stack. Normal incidence, however, corresponds to $\beta=0$, whereas for a cylindrical waveguide the desired modes typically lie near the light line $\omega=c\beta$ (in the limit of large R, the lowest-order modes are essentially plane waves propagating along z-axis, i.e., the waveguide axis). In this case, the quarter-wave condition becomes:

$$d_{hi}\sqrt{n_{hi}^2-1}=d_{lo}\sqrt{n_{lo}^2-1}=\lambda/4 \qquad (2)$$

This equation may not be exactly optimal because the quarter-wave condition is modified by the cylindrical geometry, which may require the optical thickness of each layer to vary smoothly with its radial coordinate. In addition, the differing absorption of the high and low index materials can change the optimal layer thicknesses from their quarter-wave values.

In certain embodiments, confinement region 220 includes layers that do not satisfy the quarter-wave condition given in Eq. 2. In other words, for the example shown in FIG. 2B, one or more of layers 212, 213, 214, 215, 216, 217, 218, 219, 222, and 223 are thicker or thinner than $d_{\lambda/4}$, where $$d_{\lambda/4} = \frac{\lambda}{4\sqrt{n^2-1}},$$

and n is the refractive index of the layer (i.e., $d_{\lambda/4}$ corresponds to an optical thickness equal to the quarter-wave thickness). For example, one or more layers in the confinement region can have a thickness of about 0.9 $d_{\lambda/4}$ or less (e.g., about 0.8 $d_{\lambda/4}$ or less, about 0.7 $d_{\lambda/4}$ or less, about 0.6 $d_{\lambda/4}$ or less, about 0.5 $d_{\lambda/4}$ or less, about 0.4 $d_{\lambda/4}$ or less, about 0.3 $d_{\lambda/4}$ or less), or about 1.1 $d_{\lambda/4}$ or more (e.g., about 1.2 $d_{\lambda/4}$ or more, about 1.3 $d_{\lambda/4}$ or more, about 1.4 $d_{\lambda/4}$ or more, about 1.5 $d_{\lambda/4}$ or more, about 1.8 $d_{\lambda/4}$ or more, about 2.0 $d_{\lambda/4}$ or more). In some embodiments, all layers in the confinement region can be detuned from the quarter-wave condition. In some embodiments, the thickness of one or more of the high index layers can be different (e.g., thicker or thinner) from the thickness of the other high index layers. For example, the thickness of the innermost high index layer can be different from the thickness of the other high index layers. Alternatively, or additionally, the thickness of one or more of the low index layers can be different (e.g., thicker or thinner) from the thickness of the other low index layers. For example, the thickness of the innermost low index layer can be different from the thickness of the other low index layers.

Detuning the thickness of layers in the confinement region from the quarter-wave condition can reduce the attenuation of photonic crystal fiber 120 compared to a test fiber, which refers to a fiber identical to photonic crystal fiber 120, except that the quarter-wave condition is satisfied for all layers in the confinement region (i.e., the test fiber has an identical core, and its confinement region has the same number of layers with the same composition as photonic crystal fiber 120). For example, fiber 120 can have an attenuation for one or more guided modes that is reduced by a factor of about two or more compared to the attenuation of the test fiber (e.g., reduced by a factor of about three or more, about four or more, about five or more, about ten or more, about 20 or more, about 50 or more, about 100 or more). Examples of photonic crystal fibers illustrating reduce attenuation are described in U.S. patent application Ser. No. 10/978,605, entitled "PHOTONIC CRYSTAL WAVEGUIDES AND SYSTEMS USING SUCH WAVEGUIDES," filed on Nov. 1, 2004, the entire contents of which is hereby incorporated by reference.

The thickness of each layer in the confinement region can vary depending on the composition and structure of the photonic crystal fiber. Thickness can also vary depending on the wavelength, mode, or group of modes for which the photonic crystal fiber is optimized. The thickness of each layer can be determined using theoretical and/or empirical methods. Theoretical methods include computational modeling. One computational approach is to determine the attenuation of a fiber for different layer thicknesses and use an optimization routine (e.g., a non-linear optimization routine) to determine the values of layer thickness that minimize the fiber's attenuation for a guided mode. For example, the "downhill simplex method", described in the text *Numerical Recipes in FORTRAN (second edition)*, by W. Press, S. Teukolsky, W. Vetterling, and B Flannery, can be used to perform the optimization.

Such a model should account for different attenuation mechanisms in a fiber. Two mechanisms by which energy can be lost from a guided EM mode are by absorption loss and radiation loss. Absorption loss refers to loss due to material absorption. Radiation loss refers to energy that leaks from the fiber due to imperfect confinement. Both modes of loss contribute to fiber attenuation and can be studied theoretically, for example, using transfer matrix methods and perturbation theory. A discussion of transfer matrix methods can be found in an article by P. Yeh et al., *J. Opt. Soc. Am.*, 68, p. 1196 (1978). A discussion of perturbation theory can found in an article by M. Skorobogatiy et al., *Optics Express*, 10, p. 1227 (2002). Particularly, the transfer matrix code finds propagation constants $\beta$ for the "leaky" modes resonant in a photonic crystal fiber structure. Imaginary parts of $\beta$'s define the modal radiation loss, thus $Loss_{radiation} \sim Im(\beta)$. Loss due to material absorption is calculated using perturbation theory expansions, and in terms of the modal field overlap integral it can be determined from $$Loss_{absorption} \sim 2\pi\omega \int_0^\infty r\,dr(\alpha \vec{E}_\beta^* \vec{E}_\beta), \qquad (3)$$

where $\omega$ is the radiation frequency, r is the fiber radius, $\alpha$ is bulk absorption of the material, and $\vec{E}_\beta$ is an electric field vector.

Alternatively, the desired mode fields that can propagate in the fiber can be expanded in a suitable set of functions, such as B-splines (see, e.g., *A Practical Guide to Splines*, by C. deBoor). Application of the Galerkin conditions (see, e.g., Computational Galerkin Methods, C.A.J. Fletcher, Springer-Verlag, 1984) then converts Maxwell's equations into a standard eigenvalue-eigenvector problem, which can be solved using the LAPACK software package (freely available, for example, from the netlib repository on the internet, at "http://www.netlib.org"). The desired complex propagation constants, containing both material and radiation losses, are obtained directly from the eigenvalues.

Guided modes can be classified as one of three types: pure transverse electric (TE); pure transverse magnetic (TM); and mixed modes. Loss often depends on the type of mode. For example, TE modes can exhibit lower radiation and absorption losses than TM/mixed modes. Accordingly, the fiber can be optimized for guiding a mode that experiences low radiation and/or absorption loss.

While confinement region 220A includes multiple annular layers that give rise to a radial refractive index modulation, in general, confinement regions can also include other structures to provide confinement properties. For example, referring to FIG. 2C, a confinement region 220B includes continuous layers 240 and 250 of dielectric material (e.g., polymer, glass) having different refractive indices, as opposed to multiple discrete, concentric layers. Continuous layers 240 and 250 form a spiral around axis 299. One or more of the layers, e.g., layer 240 is a high-index layer having an index $n_H$ and a thickness $d_H$, and the layer, e.g., layer 250, is a low-index layer having an index $n_L$ and a thickness $d_L$, where $n_H > n_L$ (e.g., $n_H - n_L$ can be about 0.01 or more, about 0.05 or more, about 0.1 or more, about 0.2 or more, about 0.5 or more).

Because layers 240 and 250 spiral around axis 199, a radial section extending from axis 199 intersects each of the layers more than once, providing a radial profile that includes alternating high index and low index layers.

The spiraled layers in confinement region 220B provide a periodic variation in the index of refraction along a radial section, with a period corresponding to the optical thickness of layers 240 and 250. In general, the radial periodic variation has an optical period corresponding to $n_{240}d_{240}+n_{250}d_{250}$.

The thickness ($d_{240}$ and $d_{250}$) and optical thickness ($n_{240}d_{240}$ and $n_{250}d_{250}$) of layers 240 and 250 are selected based on the same considerations as discussed for confinement region 220A above.

Figure 2C:
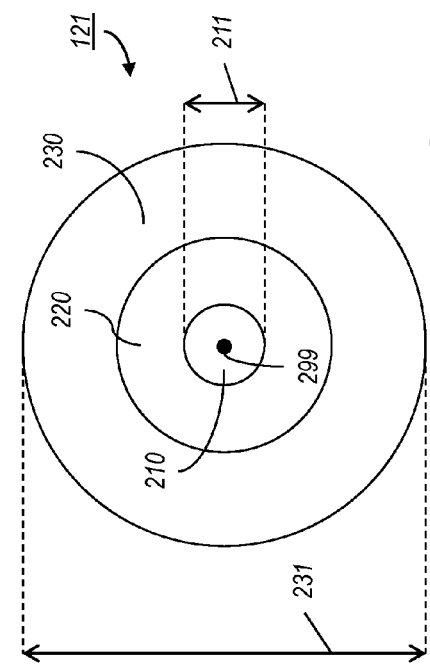

For the embodiment shown in FIG. 2C, confinement region 220B is 5 optical periods thick. In practice, however, spiral confinement regions may include many more optical periods (e.g., about 8 optical periods or more, about 10 optical periods or more, about 15 optical periods or more, about 20 optical periods or more, about 25 optical periods or more, such as about 40 or more optical periods).

Fiber's having spiral confinement regions can be formed from a spiral perform by rolling a planar multilayer film into a spiral and consolidating the spiral by fusing (e.g., by heating) the adjacent layers of the spiral together. In some embodiments, the planar multilayer film can be rolled into a spiral around a mandrel (e.g., a glass cylinder or rod), and the mandrel can be removed (e.g., by etching or by separating the mandrel from the spiral sheath and slipping it out of the sheath) after consolidation to provide the spiral cylinder. The mandrel can be formed from a single material, or can include portions of different materials. For example, in some embodiments, the mandrel can be coated with one or more layers that are not removed after consolidation of the rolled spiral structure. As an example, a mandrel can be formed from a first material (e.g., a silicate glass) in the form of a hollow rod, and a second material (e.g., another glass, such as a chalcogenide glass) coated onto the outside of the hollow rod. The second material can be the same as one of the materials used to form the multilayer film. After consolidation, the first material is etched, and the second material forms part of the fiber preform.

In some embodiments, additional material can be disposed on the outside of the wrapped multilayer film. For example, a polymer film can be wrapped around the outside of the spiral, and subsequently fused to the spiral to provide an annular polymer layer (e.g., the cladding). In certain embodiments, both the multilayer film and an additional film can be wrapped around the mandrel and consolidated in a single fusing step. In embodiments, the multilayer film can be wrapped and consolidated around the mandrel, and then the additional film can be wrapped around the fused spiral and consolidated in a second fusing step. The second consolidation can occur prior to or after etching the mandrel. Optionally, one or more additional layers can be deposited (e.g., using CVD) within the spiral prior to wrapping with the additional film.

Methods for preparing spiral articles are described in U.S. patent application Ser. No. 10/733,873, entitled "FIBER WAVEGUIDES AND METHODS OF MAKING SAME," filed on Dec. 10, 2003, the entire contents of which are hereby incorporated by reference.

Figure 2D:
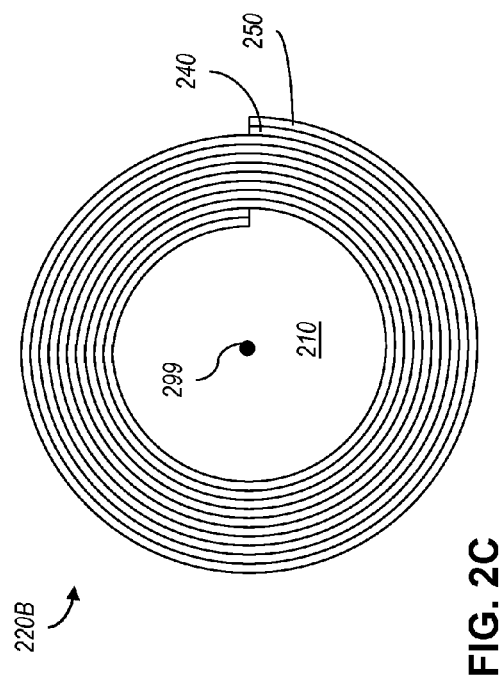

Referring to FIG. 2D, in some embodiments, photonic crystal fiber 120 can include a confinement region 220C that includes a spiral portion 260 and an annular portion 270. The number of layers in annular portion 270 and spiral portion 260 (along a radial direction from the fiber axis) can vary as desired. In some embodiments, annular portion can include a single layer. Alternatively, as shown in FIG. 2D, annular portion 270 can include multiple layers (e.g., two or more layers, three or more layers, four or more layers, five or more layers, ten or more layers).

In embodiments where annular portion 270 includes more than one layer, the optical thickness of each layer may be the same or different as other layers in the annular portion. In some embodiments, one or more of the layers in annular portion 270 may have an optical thickness corresponding to the quarter wave thickness (i.e., as given by Eq. (2). Alternatively, or additionally, one or more layers of annular portion 270 can have a thickness different from the quarter wave thickness. Layer thickness can be optimized to reduce (e.g., minimize) attenuation of guided radiation using the optimization methods disclosed herein.

In certain embodiments, annular portion 270 can be formed from materials that have relatively low concentrations of defects that would scatter and/or absorb radiation guided by photonic crystal fiber 120. For example, annular portion 270 can include one or more glasses with relatively low concentrations of inhomogeneities and/or impurities Inhomogeneities and impurities can be identified using optical or electron microscopy, for example. Raman spectroscopy, glow discharge mass spectroscopy, sputtered neutrals mass spectroscopy or Fourier Transform Infrared spectroscopy (FTIR) can also be used to monitor inhomogeneities and/or impurities in photonic crystal fibers.

In certain embodiments, annular portion 270 is formed from materials with a lower concentration of defects than spiral portion 260. In general, these defects include both structural defects (e.g., delamination between layers, cracks) and material inhomogeneities (e.g., variations in chemical composition and/or crystalline structure).

Fibers having confinement regions such as shown in FIG. 2D can be prepared by depositing one or more annular layers onto a surface of a cylinder having a spiral cross-section to form a preform. The photonic crystal fiber can then be drawn from the preform.

Annular layers can be deposited onto a surface of the spiral cylinder using a variety of deposition methods. For example, where the spiral portion is between the annular portion and the core, material can be evaporated or sputtered onto the outer surface of the spiral article to form the preform.

In embodiments where the annular portion of the photonic crystal fiber is between the spiral portion and the core, material can be deposited on the inner surface of the spiral article by, for example, chemical vapor deposition (e.g., plasma enhanced chemical vapor deposition). Methods for depositing layers of, for example, one or more glasses onto an inner surface of a cylindrical preform are described in U.S. patent application Ser. No. 10/720,453, entitled "DIELECTRIC WAVEGUIDE AND METHOD OF MAKING THE SAME," filed on Nov. 24, 2003, the entire contents of which are hereby incorporated by reference.

In general, a confinement region may include photonic crystal structures different from a multilayer configuration. For example, confinement region 220C includes both a spiral portion and annular portion, in some embodiments, confinement regions can include portions with other non-spiral structure. For example, a confinement region can include a spiral portion and a holey portion (e.g., composed of a solid cylinder perforated by a number of holes that extend along the fiber's axis). The holes can be arranged along concentric circles, providing a variation in the radial refractive index of the holey portion of the confinement region.

With regard to the composition of confinement region 220, the composition of high index and low index layers are typically selected to provide a desired refractive index contrast between the layers at the fiber's operational wavelength(s). The composition of each high index layer can be the same or different as other high index layers, just as the composition of each low index layer can be the same or different as other low index layers.

Suitable materials for high and low index layers can include inorganic materials such as inorganic glasses or amorphous alloys. Examples of inorganic glasses include oxide glasses (e.g., heavy metal oxide glasses), halide glasses and/or chalcogenide glasses, and organic materials, such as polymers. Examples of polymers include acrylonitrile-butadiene-styrene (ABS), poly methylmethacrylate (PMMA), cellulose acetate butyrate (CAB), polycarbonates (PC), polystyrenes (PS) (including, e.g., copolymers styrene-butadiene (SBC), methylestyrene-acrylonitrile, styrene-xylylene, styrene-ethylene, styrene-propylene, styrene-acylonitrile (SAN)), polyetherimide (PEI), polyvinyl acetate (PVAC), polyvinyl alcohol (PVA), polyvinyl chloride (PVC), polyoxymethylene; polyformaldehyde (polyacetal) (POM), ethylene vinyl acetate copolymer (EVAC), polyamide (PA), polyethylene terephthalate (PETP), fluoropolymers (including, e.g., polytetrafluoroethylene (PTFE), polyperfluoroalkoxythylene (PFA), fluorinated ethylene propylene (FEP)), polybutylene terephthalate (PBTP), low density polyethylene (PE), polypropylene (PP), poly methyl pentenes (PMP) (and other polyolefins, including cyclic polyolefins), polytetrafluoroethylene (PTFE), polysulfides (including, e.g., polyphenylene sulfide (PPS)), and polysulfones (including, e.g., polysulfone (PSU), polyehtersulfone (PES), polyphenylsulphone (PPSU), polyarylalkylsulfone, and polysulfonates). Polymers can be homopolymers or copolymers (e.g., (Co)poly(acrylamide-acrylonitrile) and/or acrylonitrile styrene copolymers). Polymers can include polymer blends, such as blends of polyamides-polyolefins, polyamides-polycarbonates, and/or PES-polyolefins, for example.

Further examples of polymers that can be used include cyclic olefin polymers (COPs) and cyclic olefin copolymers (COCs). In some embodiments, COPs and COCs can be prepared by polymerizing norbornen monomers or copolymerization norbornen monomers and other polyolefins (polyethylene, polypropylene). Commercially-available COPs and/or COCs can be used, including, for example, Zeonex® polymers (e.g., Zeonex® E48R) and Zeonor® copolymers (e.g., Zeonor® 1600), both available from Zeon Chemicals L.P. (Louisville, Ky.). COCs can also be obtained from Promerus LLC (Brecksville, Ohio) (e.g., such as FS1700).

Alternatively, or additionally, low-index regions may be fabricated by using hollow structural support materials, such as silica spheres or hollow fibers, to separate high-index layers or regions. Examples of fibers that include such structural supports are described in Published International Application WO 03/058308, entitled "BIREFRINGENT OPTICAL FIBRES," the entire contents of which are hereby incorporated by reference.

In certain embodiments, the confinement region is a dielectric confinement region, being composed of substantially all dielectric materials, such as one or more glasses and/or one or more dielectric polymers. Generally, a dielectric confinement region includes substantially no metal layers.

In some embodiments, the high index layers or low index layers of the confinement region can include chalcogenide glasses (e.g., glasses containing a chalcogen element, such as sulphur, selenium, and/or tellurium). In addition to a chalcogen element, chalcogenide glasses may include one or more of the following elements: boron, aluminum, silicon, phosphorus, sulfur, gallium, germanium, arsenic, indium, tin, antimony, thallium, lead, bismuth, cadmium, lanthanum and the halides (fluorine, chlorine, bromide, iodine).

Chalcogenide glasses can be binary or ternary glasses, e.g., As—S, As—Se, Ge—S, Ge—Se, As—Te, Sb—Se, As—S—Se, S—Se—Te, As—Se—Te, As—S—Te, Ge—S—Te, Ge—Se—Te, Ge—S—Se, As—Ge—Se, As—Ge—Te, As—Se—Pb, As—S—Tl, As—Se—Tl, As—Te—Tl, As—Se—Ga, Ga—La—S, Ge—Sb—Se or complex, multicomponent glasses based on these elements such as As—Ga—Ge—S, Pb—Ga—Ge—S, etc. The ratio of each element in a chalcogenide glass can be varied.

In certain embodiments, in addition or alternative to chalcogenide glass(es), one or more layers in confinement region 220 can include one or more oxide glasses (e.g., heavy metal oxide glasses), halide glasses, amorphous alloys, or combinations thereof.

In general, the absorption of the high and low index layers varies depending on their composition and on the fiber's operational wavelength(s). In some embodiments, the material forming both the high and low index layers can have low absorption. A low absorption material has absorption of about 100 dB/m or less at the wavelength of operation (e.g., about 20 dB/m or less, about 10 dB/m or less, about 5 dB/m or less, about 1 dB/m or less, 0.1 dB/m or less). Examples of low absorption materials include chalcogenide glasses, which, at wavelengths of about 3 microns, exhibit an absorption coefficient of about 4 dB/m. At wavelengths of about 10.6 microns, chalcogenide glasses exhibit an absorption coefficient of about 10 dB/m. As another example, oxide glasses (e.g., lead borosilicate glasses, or silica) can have low absorption for wavelengths between about 1 and 2 microns. Some oxide glasses can have an absorption coefficient of about 1 dB/m to 0.0002 dB/m in this wavelength range.

Alternatively, one or both of the high and low index materials can have high absorption (e.g., about 100 dB/m or more, such as about 1,000 or more, about 10,000 or more, about 20,000 or more, about 50,000 dB/m or more). For example, many polymers exhibit an absorption coefficient of about $10^5$ dB/m for wavelengths between about 3 and about 11 microns. Examples of such polymers include polyetherimide (PEI), polychlorotrifluoro ethylene (PCTFE), perfluoroalkoxyethylene (PFA), and polyethylene naphthalate (PEN). PEI has an absorption of more than about $10^5$ dB/m at 3 microns, while PCTFE, PFA, and PEN have absorptions of more than about $10^5$ dB/m at 10.6 microns.

In some embodiments, the high index material has a low absorption coefficient and the low absorption material has a high absorption coefficient, or vice versa.

A material's absorption can be determined by measuring the relative transmission through at least two different thicknesses, $T_1$ and $T_2$, of the material. Assuming the field in the material decays with thickness T according to $Pe^{-\alpha T}$, with P representing the power incident on the material, the measured transmitted power through thicknesses $T_1$ and $T_2$ will then be $P_1 = Pe^{-\alpha T_1}$ and $P_2 = Pe^{-\alpha T_2}$. The absorption coefficient $\alpha$ is then obtained as $$\alpha = -\frac{1}{T_2 - T_1} \ln(P_2/P_1).$$

If desired, a more accurate evaluation of α can be obtained by using several thicknesses and performing a least squares fit to the logarithm of the transmitted power.

As discussed previously, materials can be selected for the confinement region to provide advantageous optical properties (e.g., low absorption with appropriate indices of refraction at the guided wavelength(s)). However, the materials should also be compatible with the processes used to manufacture the fiber. In some embodiments, the high and low index materials should preferably be compatible for co-drawing. Criteria for co-drawing compatibility are provided in aforementioned U.S. patent application Ser. No. 10/121,452, entitled "HIGH INDEX-CONTRAST FIBER WAVEGUIDES AND APPLICATIONS." In addition, the high and low index materials should preferably be sufficiently stable with respect to crystallization, phase separation, chemical attack and unwanted reactions for the conditions (e.g., environmental conditions such as temperature, humidity, and ambient gas environment) under which the fiber is formed, deployed, and used.

When making a robust fiber waveguides using a drawing process, not every combination of materials with desired optical properties is necessarily suitable. Typically, one should select materials that are rheologically, thermo-mechanically, and physico-chemically compatible. Several criteria for selecting compatible materials will now be discussed.

A first criterion is to select materials that are rheologically compatible. In other words, one should select materials that have similar viscosities over a broad temperature range, corresponding to the temperatures experience during the different stages of fiber drawing and operation. Viscosity is the resistance of a fluid to flow under an applied shear stress. Here, viscosities are quoted in units of Poise. Before elaborating on rheological compatibility, it is useful define a set of characteristic temperatures for a given material, which are temperatures at which the given material has a specific viscosity.

The annealing point, $T_a$, is the temperature at which a material has a viscosity $10^{13}$ Poise. $T_a$ can be measured using a Model SP-2A System from Orton Ceramic Foundation (Westerville, Ohio). Typically, $T_a$ is the temperature at which the viscosity of a piece of glass is low enough to allow for relief of residual stresses.

The softening point, $T_s$, is the temperature at which a material has a viscosity $10^{7.65}$ Poise. $T_s$, can be measured using a softening point instrument, e.g., Model SP-3A from Orton Ceramic Foundation (Westerville, Ohio). The softening point is related to the temperature at which the materials flow changes from plastic to viscous in nature.

The working point, $T_w$, is the temperature at which a material has a viscosity $10^4$ Poise. $T_w$ can be measured using a glass viscometer, e.g., Model SP-4A from Orton Ceramic Foundation (Westerville, Ohio). The working point is related to the temperature at which a glass can be easily drawn into a fiber. In some embodiments, for example, where the material is an inorganic glass, the material's working point temperature can be greater than 250° C., such as about 300° C., 400° C., 500° C. or more.

The melting point, $T_m$, is the temperature at which a material has a viscosity $10^2$ Poise. $T_m$ can also be measured using a glass viscometer, e.g., Model SP-4A from Orton Ceramic Foundation (Westerville, Ohio). The melting point is related to the temperature at which a glass becomes a liquid and control of the fiber drawing process with respect to geometrical maintenance of the fiber becomes very difficult.

To be rheologically compatible, two materials should have similar viscosities over a broad temperature range, e.g., from the temperature at which the fiber is drawn down to the temperature at which the fiber can no longer release stress at a discernible rates (e.g., at $T_a$) or lower. Accordingly, the working temperature of two compatible materials should be similar, so that the two materials flow at similar rates when drawn. For example, if one measures the viscosity of the first material, $\eta_1(T)$ at the working temperature of the second material, $T_{w2}$, $\eta_1(T_{w2})$ should be at least $10^3$ Poise, e.g., $10^4$ Poise or $10^5$ Poise, and no more than $10^7$ Poise. Moreover, as the drawn fiber cools the behavior of both materials should change from viscous to elastic at similar temperatures. In other words, the softening temperature of the two materials should be similar. For example, at the softening temperature of the second material, $T_{s2}$, the viscosity of the first material, $\eta_1(T_{s2})$ should be at least $10^6$ Poise, e.g., $10^7$ Poise or $10^8$ Poise and no more than $10^9$ Poise. In preferred embodiments, it should be possible to anneal both materials together, so at the annealing temperature of the second material, $T_{a2}$, the viscosity of the first material, $\eta_1(T_{a2})$ should be at least $10^8$ Poise (e.g., at least $10^9$ Poise, at least $10^{10}$ Poise, at least $10^{11}$ Poise, at least $10^{12}$ Poise, at least $10^{13}$ Poise, at least $10^{14}$ Poise).

Additionally, to be rheologically compatible, the change in viscosity as a function of temperature (i.e., the viscosity slope) for both materials should preferably match as close as possible.

A second selection criterion is that the thermal expansion coefficients (TEC) of each material should be similar at temperatures between the annealing temperatures and room temperature. In other words, as the fiber cools and its rheology changes from liquid-like to solid-like, both materials' volume should change by similar amounts. If the two materials TEC's are not sufficiently matched, a large differential volume change between two fiber portions can result in a large amount of residual stress buildup, which can cause one or more portions to crack and/or delaminate. Residual stress may also cause delayed fracture even at stresses well below the material's fracture stress.

The TEC is a measure of the fractional change in sample length with a change in temperature. This parameter can be calculated for a given material from the slope of a temperature-length (or equivalently, temperature-volume) curve. The temperature-length curve of a material can be measured using e.g., a dilatometer, such as a Model 1200D dilatometer from Orton Ceramic Foundation (Westerville, Ohio). The TEC can be measured either over a chosen temperature range or as the instantaneous change at a given temperature. This quantity has the units $°C.^{-1}$.

For many materials, there are two linear regions in the temperature-length curve that have different slopes. There is a transition region where the curve changes from the first to the second linear region. This region is associated with a glass transition, where the behavior of a glass sample transitions from that normally associated with a solid material to that normally associated with a viscous fluid. This is a continuous transition and is characterized by a gradual change in the slope of the temperature-volume curve as opposed to a discontinuous change in slope. A glass transition temperature, $T_g$, can be defined as the temperature at which the extrapolated glass solid and viscous fluid lines intersect. The glass transition temperature is a temperature associated with a change in the materials rheology from a brittle solid to a solid that can flow. Physically, the glass transition temperature is related to the thermal energy required to excite various molecular translational and rotational modes in the material. The glass transition temperature is often taken as the approximate annealing point, where the viscosity is $10^{13}$ Poise, but in fact, the measured $T_g$ is a relative value and is dependent upon the measurement technique.

A dilatometer can also be used to measure a dilatometric softening point, $T_{ds}$. A dilatometer works by exerting a small compressive load on a sample and heating the sample. When the sample temperature becomes sufficiently high, the material starts to soften and the compressive load causes a deflection in the sample, when is observed as a decrease in volume or length. This relative value is called the dilatometric softening point and usually occurs when the materials viscosity is between $10^{10}$ and $10^{12.5}$ Poise. The exact $T_{ds}$ value for a material is usually dependent upon the instrument and measurement parameters. When similar instruments and measurement parameters are used, this temperature provides a useful measure of different materials rheological compatibility in this viscosity regime.

As mentioned above, matching the TEC is an important consideration for obtaining fiber that is free from excessive residual stress, which can develop in the fiber during the draw process. Typically, when the TEC's of the two materials are not sufficiently matched, residual stress arises as elastic stress. The elastic stress component stems from the difference in volume contraction between different materials in the fiber as it cools from the glass transition temperature to room temperature (e.g., 25° C.). The volume change is determined by the TEC and the change in temperature. For embodiments in which the materials in the fiber become fused or bonded at any interface during the draw process, a difference in their respective TEC's will result in stress at the interface. One material will be in tension (positive stress) and the other in compression (negative stress), so that the total stress is zero. Moderate compressive stresses themselves are not usually a major concern for glass fibers, but tensile stresses are undesirable and may lead to failure over time. Hence, it is desirable to minimize the difference in TEC's of component materials to minimize elastic stress generation in a fiber during drawing. For example, in a composite fiber formed from two different materials, the absolute difference between the TEC's of each glass between $T_g$ and room temperature measured with a dilatometer with a heating rate of 3° C./min, should be no more than about $5 \times 10^{-6}$ °C.$^{-1}$ (e.g., no more than about $4 \times 10^{-6}$ °C.$^{-1}$, no more than about $3 \times 10^{-6}$ °C.$^{-1}$, no more than about $2 \times 10^{-6}$ °C.$^{-1}$, no more than about $1 \times 10^{-6}$ °C.$^{-1}$, no more than about $5 \times 10^{-7}$ °C.$^{-1}$, no more than about $4 \times 10^{-7}$ °C.$^{-1}$, no more than about $3 \times 10^{-7}$ °C.$^{-1}$, no more than about $2 \times 10^{-7}$ °C.$^{-1}$).

While selecting materials having similar TEC's can minimize an elastic stress component, residual stress can also develop from viscoelastic stress components. A viscoelastic stress component arises when there is sufficient difference between strain point or glass transition temperatures of the component materials. As a material cools below $T_g$ it undergoes a sizeable volume contraction. As the viscosity changes in this transition upon cooling, the time needed to relax stress increases from zero (instantaneous) to minutes. For example, consider a composite preform made of a glass and a polymer having different glass transition ranges (and different $T_g$'s). During initial drawing, the glass and polymer behave as viscous fluids and stresses due to drawing strain are relaxed instantly. After leaving the hottest part of the draw furnace, the fiber rapidly loses heat, causing the viscosities of the fiber materials to increase exponentially, along with the stress relaxation time. Upon cooling to its $T_g$, the glass and polymer cannot practically release any more stress since the stress relaxation time has become very large compared with the draw rate. So, assuming the component materials possess different $T_g$ values, the first material to cool to its $T_g$ can no longer reduce stress, while the second material is still above its $T_g$ and can release stress developed between the materials. Once the second material cools to its $T_g$, stresses that arise between the materials can no longer be effectively relaxed. Moreover, at this point the volume contraction of the second glass is much greater than the volume contraction of the first material (which is now below its $T_g$ and behaving as a brittle solid). Such a situation can result sufficient stress buildup between the glass and polymer so that one or both of the portions mechanically fail. This leads us to a third selection criterion for choosing fiber materials: it is desirable to minimize the difference in $T_g$'s of component materials to minimize viscoelastic stress generation in a fiber during drawing. Preferably, the glass transition temperature of a first material, $T_{g1}$, should be within 100° C. of the glass transition temperature of a second material, $T_{g2}$ (e.g., $|T_{g1}-T_{g2}|$ should be less than 90° C., less than 80° C., less than 70° C., less than 60° C., less than 50° C., less than 40° C., less than 30° C., less than 20° C., less than 10° C.).

Since there are two mechanisms (i.e., elastic and viscoelastic) to develop permanent stress in drawn fibers due to differences between constituent materials, these mechanisms may be employed to offset one another. For example, materials constituting a fiber may naturally offset the stress caused by thermal expansion mismatch if mismatch in the materials $T_g$'s results in stress of the opposite sign. Conversely, a greater difference in $T_g$ between materials is acceptable if the materials' thermal expansion will reduce the overall permanent stress. One way to assess the combined effect of thermal expansion and glass transition temperature difference is to compare each component materials' temperature-length curve. After finding $T_g$ for each material using the foregoing slope-tangent method, one of the curves is displaced along the ordinate axis such that the curves coincide at the lower $T_g$ temperature value. The difference in y-axis intercepts at room temperature yields the strain, $\epsilon$, expected if the glasses were not conjoined. The expected tensile stress, $\sigma$, for the material showing the greater amount of contraction over the temperature range from $T_g$ to room temperature, can be computed simply from the following equation:

$$\sigma = E \cdot \epsilon, \qquad (4)$$

where E is the elastic modulus for that material. Typically, residual stress values less than about 100 MPa (e.g., about 50 MPa or less, about 30 MPa or less), are sufficiently small to indicate that two materials are compatible.

A fourth selection criterion is to match the thermal stability of candidate materials. A measure of the thermal stability is given by the temperature interval $(T_x-T_g)$, where $T_x$ is the temperature at the onset of the crystallization as a material cools slowly enough that each molecule can find its lowest energy state. Accordingly, a crystalline phase is a more energetically favorable state for a material than a glassy phase. However, a material's glassy phase typically has performance and/or manufacturing advantages over the crystalline phase when it comes to fiber waveguide applications. The closer the crystallization temperature is to the glass transition temperature, the more likely the material is to crystallize during drawing, which can be detrimental to the fiber (e.g., by introducing optical inhomogeneities into the fiber, which can increase transmission losses). Usually a thermal stability interval, $(T_x-T_g)$ of at least about 80° C. (e.g., at least about 100° C.) is sufficient to permit fiberization of a material by drawing fiber from a preform. In preferred embodiments, the thermal stability interval is at least about 120° C., such as about 150° C. or more, such as about 200° C. or more. $T_x$ can be measured using a thermal analysis instrument, such as a differential thermal analyzer (DTA) or a differential scanning calorimeter (DSC).

A further consideration when selecting materials that can be co-drawn are the materials' melting temperatures, $T_m$. At the melting temperature, the viscosity of the material becomes too low to successfully maintain precise geometries during the fiber draw process. Accordingly, in preferred embodiments the melting temperature of one material is higher than the working temperature of a second, rheologically compatible material. In other words, when heating a preform, the preform reaches a temperature at it can be successfully drawn before either material in the preform melts.

One example of a pair of materials which can be co-drawn and which provide a photonic crystal fiber waveguide with high index contrast between layers of the confinement region are $As_2Se_3$ and the polymer PES. $As_2Se_3$ has a glass transition temperature ($T_g$) of about 180° C. and a thermal expansion coefficient (TEC) of about $24 \times 10^{-6}$/° C. At 10.6 µm, $As_2Se_3$ has a refractive index of 2.7775, as measured by Hartouni and coworkers and described in *Proc. SPIE*, 505, 11 (1984), and an absorption coefficient, $\alpha$, of 5.8 dB/m, as measured by Voigt and Linke and described in "Physics and Applications of Non-Crystalline Semiconductors in Optoelectronics," Ed. A. Andriesh and M. Bertolotti, NATO ASI Series, 3. High Technology, Vol. 36, p. 155 (1996). Both of these references are hereby incorporated by reference in their entirety. PES has a TEC of about $55 \times 10^{-6}$/° C. and has a refractive index of about 1.65.

Embodiments of photonic crystal fibers and methods for forming photonic crystal fibers are described in the following patents and patent applications: U.S. Pat. No. 6,625,364, entitled "LOW-LOSS PHOTONIC CRYSTAL WAVEGUIDE HAVING LARGE CORE RADIUS;" U.S. Pat. No. 6,563,981, entitled "ELECTROMAGNETIC MODE CONVERSION IN PHOTONIC CRYSTAL MULTIMODE WAVEGUIDES;" U.S. patent application Ser. No. 10/057,440, entitled "PHOTONIC CRYSTAL OPTICAL WAVEGUIDES HAVING TAILORED DISPERSION PROFILES," and filed on Jan. 25, 2002; U.S. patent application Ser. No. 10/121,452, entitled "HIGH INDEX-CONTRAST FIBER WAVEGUIDES AND APPLICATIONS," and filed on Apr. 12, 2002; U.S. Pat. No. 6,463,200, entitled "OMNI-DIRECTIONAL MULTILAYER DEVICE FOR ENHANCED OPTICAL WAVEGUIDING;" Provisional 60/428,382, entitled "HIGH POWER WAVEGUIDE," and filed on Nov. 22, 2002; U.S. patent application Ser. No. 10/196,403, entitled "METHOD OF FORMING REFLECTING DIELECTRIC MIRRORS," and filed on Jul. 16, 2002; U.S. patent application Ser. No. 10/720,606, entitled "DIELECTRIC WAVEGUIDE AND METHOD OF MAKING THE SAME," and filed on Nov. 24, 2003; U.S. patent application Ser. No. 10/733,873, entitled "FIBER WAVEGUIDES AND METHODS OF MAKING SAME," and filed on Dec. 10, 2003. The contents of each of the above mentioned patents and patent applications are hereby incorporated by reference in their entirety.

Referring again to FIG. 1, laser system 100 also includes a cooling apparatus 170, which delivers a cooling fluid (e.g., a gas or a liquid) to fiber 120 via a delivery tube 171 and coupling assembly 130. The cooling fluid is pumped through the core and absorbs heat from the fiber surface adjacent the core. In the present embodiment, the cooling fluid flows in the same direction as the radiation from laser 110, however, in some embodiments, the cooling fluid can be pumped counter to the direction of propagation of the laser radiation.

The flow rate of the cooling fluid through the core of photonic crystal fiber 120 can vary as desired. Typically, the flow rate depends on the operating power of the laser, the absorption of the fiber at the operating wavelength, the length of the fiber, and the size of the fiber core, for example. Generally, the flow rate should be sufficient to cool the fiber at its operating power. In some embodiments, the flow rate can be about 0.1 liters/min or more (e.g., about 0.5 liters/min or more, about 1 liter/min or more, about 2 liters/min or more, about 5 liters/min or more, about 8 liters/min or more, about 9 liters/min or more, about 10 liters/min or more).

The pressure of cooling fluid exhausted from the fiber can vary. In some embodiments, the pressure of the cooling fluid can be relatively high. For example, where the fluid exits from the same end of the fiber as the radiation, a cooling gas can be at sufficiently high pressure to clear debris from the target tissue of the patient. The gas pressure can be about 0.2 PSI or more (e.g., about 0.5 PSI or more, about 1 PSI or more). In some embodiments, the pressure of a gas exiting the core of a fiber can correspond to a flow rate of about 1 liter/min or more (e.g., about 2 liter/min or more, about 5 liter/min or more, about 8 liter/min or more, about 10 liter/min or more) through a 1 meter length of fiber having a core diameter of about 500 µm.

The flow rate can be nominally constant while the system is activated, or can vary depending on the state operation of the laser system. For example, in some embodiments, the flow rate can be adjusted based on whether radiation is being directed through fiber 120 or not. At times where the laser is activated and radiation is directed through the fiber, the flow rate can be at a level sufficient to adequately cool the fiber. However, between radiation doses, the system can reduce the flow rate to a lower level (e.g., about 10% or less than the rate used to cool the fiber while the laser is activated). The gas flow rate can be triggered using remote control 152 or an additional remote control that the operator can easily operate while using the system.

In general, the temperature of the cooling fluid directed to the fiber can vary. In some embodiments, the cooling fluid is directed to the fiber at ambient temperature (e.g., at room temperature). In certain embodiments, the cooling fluid is cooled below ambient temperature prior to cooling the fiber. The cooling fluid can be cooled so that fluid exhausted from the fiber is within a certain temperature range. For example, the cooling fluid can be sufficiently cooled so that fluid exhausted from the fiber does not scald the patient if it comes into contact with the patient. As another example, the cooling fluid can be sufficiently cooled so that fluid exhausted from the fiber is between room temperature and body temperature. In some embodiments, the cooling fluid directed to the fiber can be cooled so that it has a temperature below room temperature. For example, the fluid can have a temperature of about 20° C. or less (e.g., about 10° C. or less, about 0° C. or less, about –10° C. or less, about –20° C. or less, about –50° C. or less).

In certain embodiments, where the cooling fluid flows through the fiber core in the laser radiation propagation direction, it can perform additional functions where it impinges on the target tissue of the patient. For example, in some embodiments, heated fluid (e.g., gas) exiting the fiber can reduce bleeding at incised blood vessels (or other tissue) by enhancing coagulation of the blood. It is believed that coagulation of blood is accelerated at temperatures of about 60° C. or more. Accordingly, where the gas exiting the fiber impinging the target tissue is about 60° C. or more, it can increase the rate at which blood coagulates, which can assist the surgeon by reducing the need to suction blood from the operating area. In some embodiments, the temperature of gas exiting the fiber can be, for example, about 50° C. or more, about 60° C. or more, about 65° C. or more, about 70° C. or more, about 80° C. or more, about 90° C. or more, about 100° C. or more). Alternatively, in certain embodiments, the temperature of the gas exiting the fiber can be below room temperature (e.g., about 10° C. or less, about 0° C. or less). For example, the system can provide cooled gas to the target location in procedures where it is beneficial to cool tissue before irradiating the tissue. In certain embodiments, the temperature of gas exiting the fiber can be approximately at body temperature (e.g., at about 37° C.), Gas flowing through the fiber core can be heated by about 5-10° C./Watt of input power (e.g., about 7-8° C./Watt). For example, a fiber having an input power of about 20 Watts could heat gas flowing through its core by about 100-200° C.

In some embodiments, the fluid flowing through the fiber's core can be used to deliver other substances to the target tissue. For example, atomized pharmaceutical compounds could be introduced into a gas that is flowed through the core and delivered via the photonic crystal fiber to the target tissue.

In general, the type of cooling fluid can vary as desired. The cooling fluid can be liquid, gas, or superfluid. In some embodiments, the cooling fluid includes a noble gas (e.g., helium, neon, argon, krypton, and/or xenon), oxygen, carbon dioxide, and/or nitrogen. The cooling fluid can be composed substantially of a single compound (e.g., having a purity of about 98% or more, about 99% or more, about 99.5% or more, about 99.8% or more, about 99.9% or more), or can be a mixture (e.g., air or heliox).

In some embodiments, the cooling fluid is selected based on its ability to cool the fiber. The cooling ability of a fluid can depend on the fluids flow rate and/or the fluids thermal conductivity. Helium gas, for example, has a relatively high thermal conductivity compared to other gases. Furthermore, for a given pressure drop, helium can have a higher flow rate than other gases, such as nitrogen. Accordingly, in some embodiments, helium can be selected based on its ability to cool the fiber better than other gases.

Alternatively, or additionally, the cooling fluid can be selected based on whether or not it has any adverse interactions with the patient. For example, in embodiments where the cooling fluid is in close proximity to the patient, it can be selected based on its relatively low toxicity. In certain embodiments, a cooling fluid can be selected based on its solubility compared to other fluids. A fluid with relatively low solubility in blood can reduce the risk of the patient having an embolism due to exposure to the cooling fluid. An example of a fluid with relatively low toxicity and relatively low solubility is helium gas.

The cooling fluid can also be selected based on other criteria, such as its reactivity with other elements (e.g., flammability). In some embodiments, a cooling fluid, such as helium, can be selected based on its inert characteristics (e.g., inflammability).

Various embodiments of two-part conduits are described below.

In some embodiments, the two-part conduit includes a flexible waveguide (e.g., a photonic crystal fiber, such as an OmniGuide photonic crystal fiber) and a rigid ceramic tip where both the fiber and the tip have wave-guiding properties at the laser wavelength. For example, the tip can be formed from $Al_2O_3$ in the form of sapphire or alumina which can both be used with a laser wavelength of 10.6 microns. While the fiber provides a flexible conduit for the laser energy to the target, the ceramic tip at the end of the fiber provides a robust element that protects the fiber end facet against tissue debris, fluids splashes, and backscattered laser radiation. Many ceramics have a high damage threshold, for example, and can protect the fiber end facet, e.g., where the device tip is used to manipulate tissue mechanically without danger of damaging the fiber end facet.

FIGS. 3A and 3B shows a design of distal portion incorporating a flexible fiber 310 (e.g., an OmniGuide photonic crystal fiber) and a ceramic tip 330. Ceramic tip 330 is a ceramic tube with ID and OD matching those of fiber 310, facilitating optical coupling of the laser radiation between the two. The conduit also includes a braid 320 (e.g. a metallic braid, such as stainless steel, which can act as a heat sink or heat diffuser), which surrounds a portion of the ceramic tip and fiber. Ceramic tip 330 is attached to braid 320 by an adhesive 340 (e.g., a high-temperature high-strength adhesive, e.g., epoxy Epotek 353ND). Braid 320 extends over fiber 310 for a certain length, e.g., determined by mechanical strength and laser safety considerations, e.g., from 2 cm to all the way to the proximal end of the fiber. High mechanical strength of the metallic braid and multiplicity of separate strands of the braid can contribute to reliability of ceramic tip 330 attachment under possible fiber failure during laser power transmission. In some embodiments, multiple adhesive junction points between the braid and the fiber can be utilized for increased reliability.

Optical alignment of tip and fiber can be maintained by one or more mechanisms including, e.g., braid tension, choice of braid pick count, and rigidity of the braid achieved by using a rigid adhesive which encapsulates braid strands and thus renders the braid rigid. Referring specifically to FIG. 3B, alternatively, or additionally, a tubular element 350 can be positioned over the interface between fiber 310 and ceramic tip 330 or a combination of braid, adhesive and tubular element. The tubular element can be, e.g., metallic or plastic and the plastic can be heat-shrink tubing.

Referring to FIGS. 4A and 4B, in some embodiments, a flexible fiber 410 (e.g., an OmniGuide photonic crystal fiber) and a ceramic tip 440 are enclosed in a flexible mechanically-robust jacket 420, 430 extending, e.g., from the proximal end of the conduit to the distal tip. The jacket can be made of a high-temperature, high-strength material (e.g., a polyimide). In some embodiments, jacket 420 is braid-reinforced, incorporating metallic braid for, e.g., additional strength and flexibility characteristics. Varying braid wire thickness, braid pick count and jacket wall thickness allows adjusting mechanical properties of the device while using the same fiber and ceramic tip. Ceramic tip 440 can be attached directly to jacket 420, 430 in which case the jacket holds both fiber 410 and tip 440 in alignment.

In some embodiments, the ceramic tip can be recessed into the jacket and holes 510 made in the jacket in front of the tip, as shown in FIGS. 5A and 5B. Such configuration can be useful when gas is flowed through the fiber core. Gas flow is used, e.g., for clearing tissue debris and blood during tissue cutting, for cooling fiber 410 and for therapeutic reasons such as assisting tissue coagulation. Vent holes in the jacket can provide an alternative route for the gas flow in case when the device is pressed against target.

Alternatively, a ceramic tip can be joined with a flexible fiber using junction elements, for example, a single tubular element or stepwise elements in which case the ceramic tip can be of different OD than the fiber, e.g. smaller diameter. Smaller diameter tips can allow tip access to tighter spaces or passing through narrow distal opening of delivery tools used together with the device. FIGS. 6A and 6B show such embodiments. Here, the conduits include ceramic tip 620 connected to fiber 610 by way of step-wise tubular elements 650 and 640. The ceramic tip can be connected directly to the fiber with adhesive and optical alignment between the fiber and the tip is well maintained. Such assembly can also be encased into a jacket 630 similarly to the designs discussed above, where the jacket can be simple plastic tubing or braid-reinforced tubing. Varying braid wire thickness, braid pick count and tubing wall thickness allows adjusting mechanical properties of the device from the tip to the proximal connector.

In some embodiments, metallic braid is used to hold the tip and flexible fiber together and the both the tip and fiber are encased in a jacket similar to the designs described above, as illustrated in FIGS. 7A and 7B. Here, fiber 710 and tip 720 are surrounded, at least partially, by metallic braid 740 and a jacket 730, which surrounds part of the braid. The jacket can be simple plastic tubing or braid-reinforced tubing. Varying braid wire thickness, braid pick count and tubing wall thickness allows adjusting mechanical properties of the device from the tip to the proximal connector. Adhesives can be used to create junctions between the ceramic tip, the braid and the fiber. In addition, the tip/braid/fiber subassembly can be joined to the jacket by means of adhesive. Adhesive can be applied in at multiple points along the length of the device. The braid can be terminated at a certain length from the tip or run all the way to the proximal connector end of the fiber. Such designs can provide a high degree of mechanical reliability and laser safety during operation and in case of fiber failure. In certain embodiments, tip 720 is recessed in the jacket and holes 750 made in the jacket in front of the tip for applications with gas flow through the device as already described above.

In general, ceramic tips can be made using a variety of methods. For example, ceramic tips can be produced by extrusion process, grinding and molding. Molding processes can allow fabricating complex shapes of ceramic with high precision and gives additional design options to improve further functionality and/or performance of two-part fiber device.

Figure 8A:
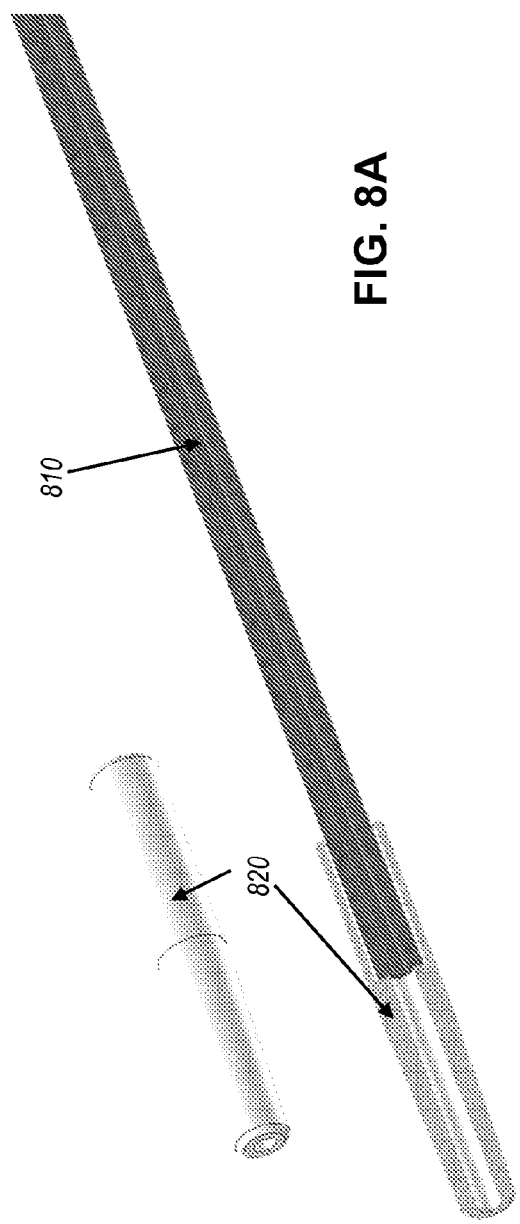
FIGS. 8A and 8B are exemplary embodiments of two-part conduits.

In some embodiments, the ceramic tip is molded into shapes that make it possible to attach the tip directly to the fiber and achieving better optical alignment enabling more consistent coupling between the flexible fiber and the tip and thus more consistent output power, higher reliability under mechanical stresses such as bending of the distal end portion of the device. The ceramic tip can be shaped on the outside to have smaller tip diameter than possible within mechanical, optical and reliability constraints for the flexible fiber and thus enabling easier insertion into delivery tools, better visualization of the target spot at the tip of the device, and greater precision. FIG. 8A shows an illustration to this design. Here, tip 820 includes a section that has an inner diameter sized to accommodate the outer diameter of fiber 810. Once attached to fiber 810, the section ensures the core of the fiber and the core of the tip are in good alignment.

Figure 8B:
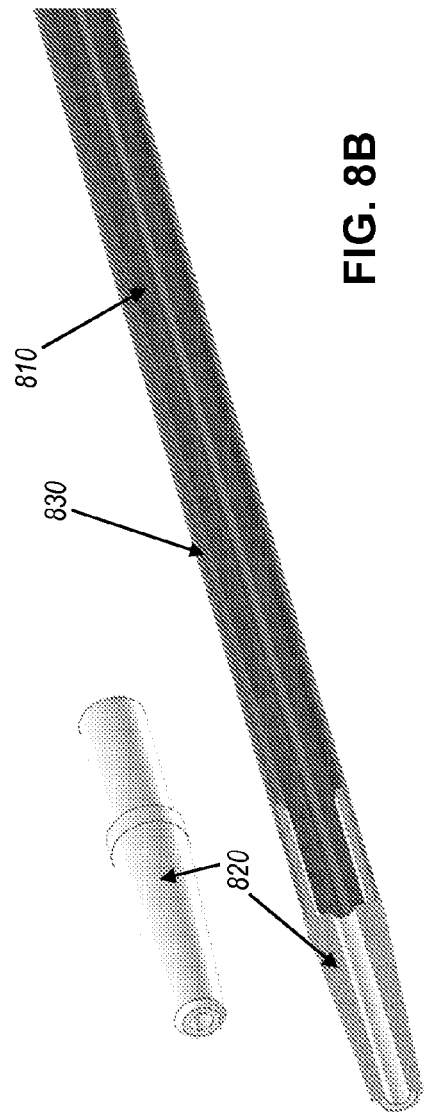

The attachment of the tip to the fiber can be accomplished in a variety of different ways: adhesive, thread if the fiber end is threaded, or through a jacket if fiber is encased into jacket, as illustrated in FIG. 8B. Here, a jacket 830 encases fiber 810 and a portion of tip 820. As illustrated in FIG. 8B, the outside of tip 820 is shaped to make the device smooth on the outside with gradual change in OD, making it better suited for insertion into narrow channel guiding and delivery instruments. Internally, tip 820 is shaped to fit securely onto the end of fiber 810 and provide good alignment between the tip and fiber cores.

Figure 9:
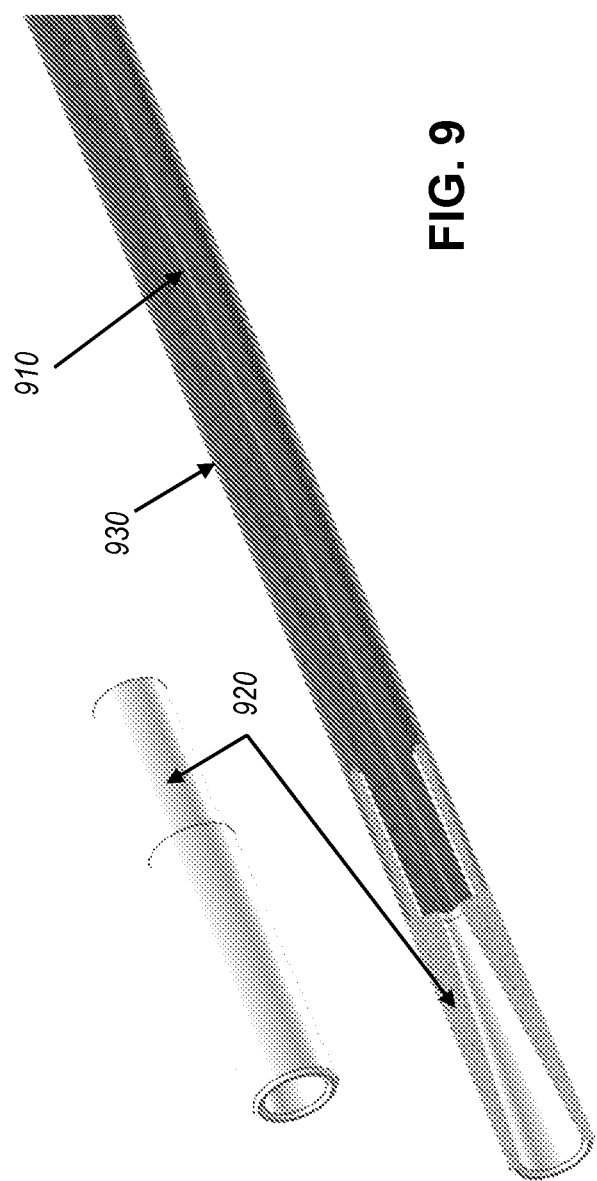
FIG. 9 is an exemplary embodiment of a two-part conduit.

The ceramic tip can be molded to have different shapes on the inside as well. For example, the ceramic tip can have a tapered core (e.g., one that increases or decreases in diameter from the output end of the fiber). Referring to FIG. 9, in some embodiments, the core of a ceramic tip 920 is conical, in which case the tip allows expansion of the output beam spot size and enabling larger spot size at the distal end of two part device. Here, the core of tip 920 increases in diameter from the tips interface with a fiber 910, where the tip's core and the fiber's core have the same diameter. Fiber 910 and a portion of tip 920 are encased in a jacket 930.

In general, the tip designs discussed above in no way are limited to rigid ceramics. A variety of other materials or structures with waveguiding properties can be engineered to make the tip with required mechanical and optical characteristics. For example, a hollow metal waveguide (e.g., silver or gold) can be used in all the designs presented above. In some embodiments, waveguides are composed of a hollow dielectric (e.g., polymer or glass, such as silica) tube with a metallic reflective coating in the inner surface of the tube (e.g., gold or silver). Typically, the metal should have high reflectivity at the guided wavelength(s). In certain embodiments, a dielectric coating can be applied to the inner surface of the metallic coating. Dual metallic plus dielectric coatings can be used to enhance wave-guiding and reduce optical loss. Metallic silver coating with silver-iodide dielectric coating on top is well known in the art. Examples of hollow IR waveguides are described, e.g., in "A Review of IR Transmitting, Hollow Waveguides," JAMES A. HARRINGTON, Fiber and Integrated Optics, 19, 211-217 (2000), which is incorporated herein by reference.

FIG. 12A shows an embodiment of a two-part conduit 1201 that includes a flexible fiber waveguide 1210 (e.g., Omniguide fiber) and a rigid hollow waveguide tip 1202, made of highly reflective solid metal such as silver or gold. Such waveguide tips can have high mechanical strength and high thermal damage threshold relative to flexible fiber waveguide 1210, thereby protecting fiber waveguide 1210.

Waveguide tip 1202 can be shaped on the outside to have smaller tip OD than may otherwise be possible within mechanical, optical and reliability constraints for flexible fiber waveguide 1210. This smaller tip diameter may advantageously allow a user to insert conduit 1201 into a delivery tool, may provide better visualization of the target spot at the tip of the device, and/or greater precision in delivery of radiation to the target. For example, the OD of tip 1202 can be 90% or less (e.g., 80% or less, 70% or less, 60% or less, 50% or less) of the OD of fiber waveguide 1210.

In some embodiments, waveguide tip 1202 can be shaped on the inside to facilitate reliable optical and mechanical coupling with the flexible fiber waveguide. For example, waveguide tip 1202 can include portions having different inner diameters, where one portion is sized to slip over the outer diameter of fiber waveguide 1210 and another portion having the same or similar diameter as the core diameter of fiber waveguide 1210.

In general, waveguide tip 1202 can be formed from a pure metal or an alloy. For example, the tip can be formed from sterling silver (92.5% Ag/7.5% Cu).

Waveguide tips can be produced by 1202 can be formed from machining, stamping, electroforming or powder metallurgy processes.

In some embodiments, a dielectric coating can be provided on the inner surface of waveguide tip 1202. For example, a waveguide tip can be formed from silver or a silver alloy and can include a layer of silver iodide on its inner surface. It is believed that such coatings may enhance the waveguiding properties of waveguide tip 1202. See, e.g., "Optical properties of small-bore hollow glass waveguides", Y. Matsuura, T. Abel, and J. A. Harrington, Applied Optics, v. 34 (1995), p. 6842-6847.

Dielectric coatings inside a metallic waveguide tip can be produced, e.g., by solution coating process, pumping chemical solution though the core of the tips (e.g. iodine solution for silver tips). Generally, a variety of dielectric materials can be used, such as metal halides or polymers. Typically, the dielectric material should have relatively low absorption at the guided wavelength(s).

Referring to FIG. 12B, in some embodiments, fiber waveguide 1210 includes a jacket 1220 made of a high-temperature, high-strength material (e.g. polyimide). Such a jacket can be used to control mechanical properties of the conduit. The jacket can be simple plastic tubing or braid-reinforced tubing. Varying braid wire thickness, braid pick count and tubing wall thickness allows adjustment of mechanical properties of the device from the tip to the proximal end of the conduit.

Waveguide tip 1202 can be attached to both fiber 1210 and to jacket 1220, providing additional safety and reliability of the conduit. Referring to FIG. 12C, in some embodiments, waveguide tip 1202 is recessed into jacket 1220 and vent holes 1230 are provided in jacket 1220 in front of the tip. Such configurations can be useful when gas is flowed through the conduit's core.

Adhesives can be used to bond the waveguide tip, the jacket and the flexible fiber. In embodiments, waveguide tip 1202 can be bonded to fiber 1210 and to jacket 1220 separately, using either the same adhesive or different adhesives. Adhesives can be applied at multiple points along the length of the conduit. Such designs can provide a high degree of mechanical reliability and laser safety during operation and in case of fiber failure.

Figure 13:
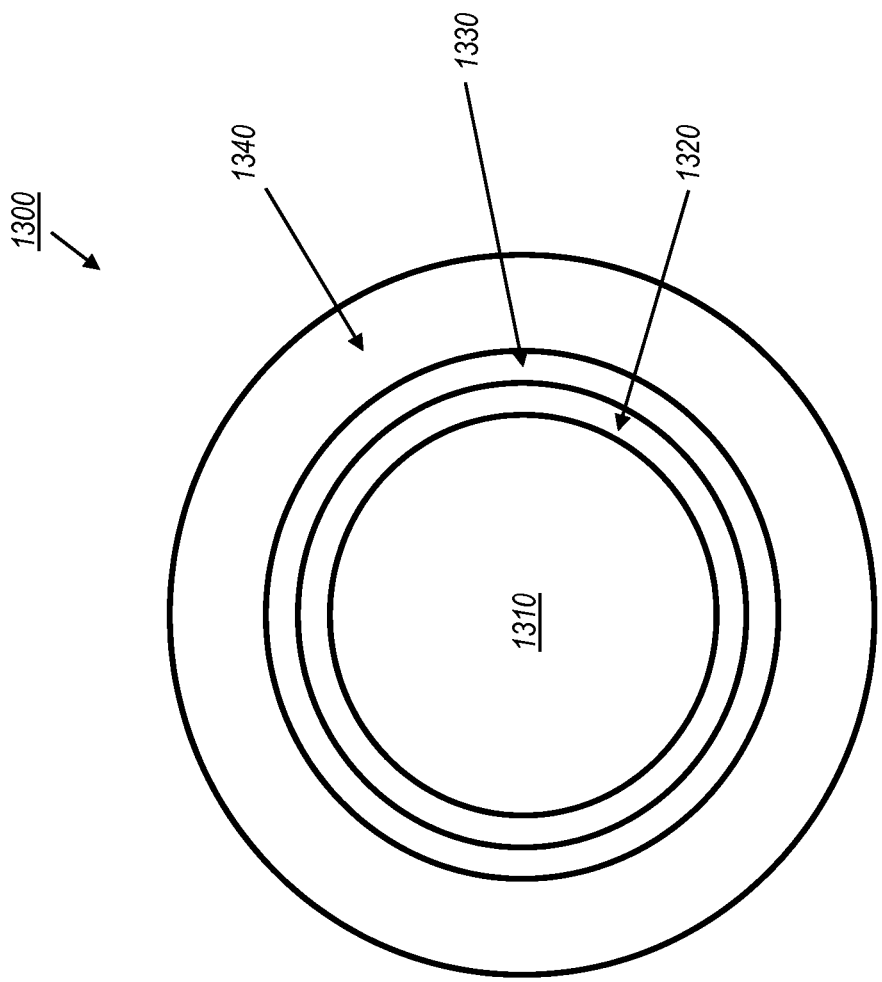
FIG. 13 is a cross-section view of an embodiment of a hollow waveguide.

Referring to FIG. 13, in some embodiments, a tip 1300 of a two-part conduit is a waveguide formed from a dielectric tube 1340 having a hollow core 1310. Dielectric tube 1340 has a metallic layer 1330 on its inner surface, and a dielectric layer 1320 on the inner surface of metallic layer 1330. For example, tip 1300 can be composed of a silica tube coated inside with thin metal (e.g., silver or gold) layer and thin dielectric on top of metal and coated on the outside with thin polymer coating (e.g., polyimide) to protect the silica tube. Generally, the metal should have a high reflectivity at the guided wavelength. Such layered structure waveguides can have good waveguiding properties, e.g., at wavelengths of 10.6 μm. Such fibers are also available commercially, e.g., the Hollow Silica Waveguide from Polymicro Technologies.

In general, the diameter of core 1310 and thickness of layers 1320 and 1330 are selected so that tip 1300 guide light at a particular wavelength and provides an output spot of a desired size. Core 1310 can have a diameter in a range from 100 μm to 1 mm (e.g., in a range from 600 μm to 800 μm). In some embodiments, the diameter of core 1310 is the same as the diameter of the core of the fiber waveguide portion of the conduit. Dielectric layer 1320 can have a thickness from 0.1 μm to 10 μm. Metal layer 1330 can have a thickness from 0.5 μm to 20 μm.

A silica tube protected with outer polymer coating can have high mechanical strength, high thermal damage threshold and at the same time can be flexible, the tip can be made to small diameters by reducing wall thickness substantially and at the same time be flexible and bendable to smaller radius, enabling a number of unique tip characteristics of the two part device. First, the tip provides a robust means of protecting the fiber end facet against tissue debris, fluids splashes, and backscattered laser radiation and allows protection of the fiber end facet to the extent that the tip can be used to manipulate tissue mechanically without danger of damaging the optical fiber end facet. Second, smaller tip profile (outside diameter) provides better visualization of the target spot at the tip of the device and greater surgical precision, as well as easier insertion into delivery tools. Finally, the tip is flexible, making possible tip manipulation and guidance of the output laser beam with greater precision right at the distal end while maintaining flexibility characteristics of the fiber portion of the device optimized for laser radiation delivery from the laser to the target over longer length.

Figure 10A:
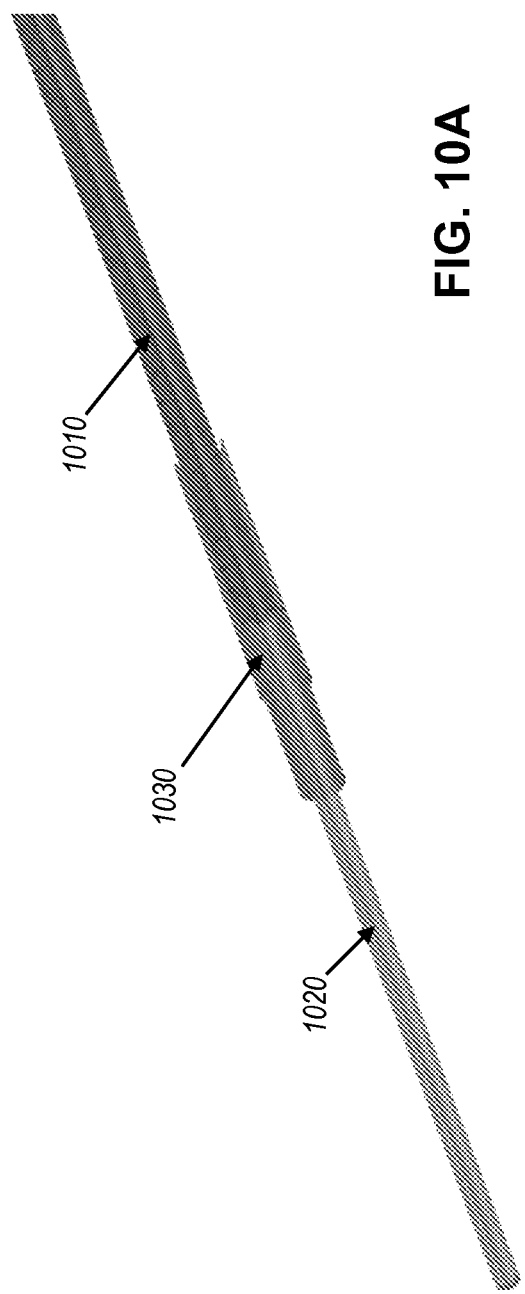

A dielectric-metallic hollow waveguide tip can be attached to the fiber using one or more junction elements, which keep optical alignment between the fiber and the tip as well as provide necessary mechanical robustness. FIG. 10A illustrates this embodiment. A tip 1020, a junction element 1030 and a fiber 1010 can be assembled using high strength adhesive (e.g., epoxy Epotek 353ND).

Referring to FIG. 10B, in some embodiments, fiber 1010 is enclosed into a jacket 1040, e.g., simple plastic tubing or braid-reinforced tubing, in similar manners as already discussed above, to provide additional mechanical strength, improve laser safety and reliability and give additional control of flexibility by means of wall thickness and braid count in the jacket adjustments. Varying braid wire thickness, braid pick count and tubing wall thickness allows changing mechanical properties of the device from the tip to the proximal connector.

For enhanced mechanical reliability, junction elements such as braid or solid tubing pieces can be used, where the adhesives can be used to bond the tip and the fiber through junction elements and in addition adhesives can be used to bond the tip junction to the jacket and fiber to the jacket in one, two or many points along the length of the device.

Referring to FIG. 10C, in cases when the tip flexibility is not needed or even can be a disadvantage, the waveguide can be encased into a thin wall metallic tube 1050.

Referring to FIG. 11A, in some embodiments, tip 1020 can be pre-bent 1060 to a particular configuration. Pre-bent configurations can be useful in procedures where access to the target tissue is limited and does not have a straight path. In general, the bend angle and bend radius will depend on the specific needs of the application and limitations of the waveguide used for the tip. In some embodiments, the tip can be adjustably bend by, e.g., the surgeon, on a patient-by-patient basis.

In general, dielectric—metallic hollow waveguide tip designs described above can incorporate jackets as shown in FIGS. 11A and 11B and discussed above in regard to FIGS. 12B and 12C.

Other types of waveguide are also contemplated. For example, in some embodiments, either the proximal or distal portions are formed from a sapphire tube (see, e.g., U.S. Pat. No. 5,030,217).

Properties of different waveguides that can be used in a conduit are shown in TABLE 1, below. Embodiments can use the waveguides listed therein.

| Property | Alumina Ceramic, glass or crystal tube | Diamond (solid core) | Metallic hollow waveguide | Metallic hollow waveguide with dielectric coating | PCF high index contrast | Solid Silica with metal/ dielectric coating | OG Multilayer dielectric waveguides |
|---|---|---|---|---|---|---|---|
| Available from: | Coors St. Gobain | DeBeers | Luxar Flexiguide | — | University of Bath, UK and NRL, USA | Polymicro | OmniGuide, Inc. |

-continued

| Property | Alumina Ceramic, glass or crystal tube | Diamond (solid core) | Metallic hollow waveguide | Metallic hollow waveguide with dielectric coating | PCF high index contrast | Solid Silica with metal/dielectric coating | OG Multilayer dielectric waveguides |
|---|---|---|---|---|---|---|---|
| Approx. Melting point (° C.) | 2000 | >4000 | Up to 1500 | 900-1600 | Up to 500 | 900-1600 | 200-300 |
| Flexibility, approx. radius of curvature (cm) | Not flexible. Limited bendability | Not flexible | 5-10 cm | 5-10 cm | | 1 cm | 1 cm |
| Approx. optical loss in dB/m at 10.6 microns | <1.0 dB, short pieces up to 5 cm length | | <2.5 dB, short pieces up to 5 cm length | 1-2 dB/m depending on the core size (300-500 μm range) | | 0.8-2 dB/m depending on the core size (300-500 μm range) | 0.25-1 dB/m depending on the core size (300-500 μm range) |
| Approx. optical loss in dB/m at 2 microns | | | | 2-2.5 dB/m depending on the core size (300-500 μm range) | | 1.5-2 dB/m depending on the core size (300-500 μm range) | |
| Method of Manufacture | Molding Mechanical machining Draw/Extrusion | Mechanical machining | Process 2-3 meters at a time | Process 2-3 meters at a time | Draw at tens of meters per run | Draw and liquid chemistry. Process 2-3 meters at a time | Draw hundreds of meters per run, scalable |
| Comparative Manufacturing Cost | Low | Very High | Medium | Medium to High | High | High | Medium |

In some cases, a handpiece in a medical laser system can be replaced by a robot, which can be operated remotely. For example, robot-performed surgery is under consideration in applications where a surgeon cannot easily or rapidly reach a patient (e.g., a wounded soldier on a battlefield).

Since the described conduits are used in medical procedures, they should be sterilizable. For example, conduits should be able to withstand sterilizing procedures, such as autoclaving. Typically, conduits are provided to the user pre-sterilized and sealed in a container (e.g., vacuum sealed in a container that has sufficient barrier properties to prevent contamination of the conduit length during storage and shipping). For example, sterilized lengths of conduit (e.g., about 0.5 meters to about 2.5 meters lengths) can be provided sealed (e.g., vacuum sealed) in a plastic container (e.g., including a barrier film layer).

In general, the laser systems described above can be used in a number of different medical applications. Generally, the type of laser, wavelength, fiber length, fiber outer diameter, and fiber inner diameter, among other system parameters, will be selected according to the application. Medical applications include aesthetic medical procedures, surgical medical procedures, ophthalmic procedures, veterinary procedures, and dental procedures.

Aesthetic procedures include treatment for: hair removal; pulsed light skin treatments for reducing fine wrinkle lines, sun damage, age spots, freckles, some birthmarks, rosacea, irregular pigmentation, broken capillaries, benign brown pigment and pigmentation; skin resurfacing; leg veins; vascular lesions; pigmented lesions; acne; psoriasis & vitiligo; and/or cosmetic repigmentation.

Surgical procedures include procedures for gynecology, laparoscopy, condylomas and lesions of the external genitalia, and/or leukoplakia. Surgical applications can also include ear/nose/throat (ENT) procedures, such as laser assisted uvula palatoplasty (LAUP) (i.e., to stop snoring); procedures to remove nasal obstruction; stapedotomy; stapedectomy; tracheobronchial endoscopy; tonsil ablation; and/or removal of benign laryngeal lesions. Surgical applications can also include breast biopsy, cytoreduction for metastatic disease, treatment of decubitus or statis ulcers, hemorrhoidectomy, laparoscopic surgery, mastectomy, and/or reduction mammoplasty. Surgical procedures can also include procedures in the field of podiatry, such as treatment of neuromas, periungual, subungual and plantar warts, porokeratoma ablation, and/or radical nail excision. Other fields of surgery in which lasers may be used include orthopedics, urology, gastroenterology, thoracic & pulmonary surgery, and neurosurgery.

Ophthalmic uses include treatment of glaucoma, age-related macular degeneration (AMD), proliferative diabetic retinopathy, retinopathy of prematurity, retinal tear and detachment, retinal vein occlusion, and/or refractive surgery treatment to reduce or eliminate refractive errors.

Veterinary uses include both small animal and large animal procedures.

Examples of dental applications include hard tissue, soft tissue, and endodontic procedures. Hard tissue dental procedures include caries removal & cavity preparation and laser etching. Soft tissue dental procedures include incision, excision & vaporization, treatment of gummy smile, coagulation (hemostasis), exposure of unerupted teeth, aphthous ulcers, gingivoplasty, gingivectomy, gingival troughing for crown impressions, implant exposure, frenectomy, flap surgery, fibroma removal, operculectomy, incision & drainage of abscesses, oral papillectomy, reduction of gingival hypertrophy, pre-prosthetic surgery, pericoronitis, peri implantitis, oral lesions, and sulcular debridement. Endodontic procedures include pulpotomy, root canal debridement, and cleaning Dental procedures also include tooth whitening.

Generally, the type of laser, wavelength, conduit length, conduit outer diameter, and conduit inner diameter, among other system parameters, are selected according to the application. For example, embodiments in which the laser is a $CO_2$ laser, the laser system can be used for surgical procedures requiring the ablation, vaporization, excision, incision, and coagulation of soft tissue. $CO_2$ laser systems can be used for surgical applications in a variety of medical specialties including aesthetic specialties (e.g., dermatology and/or plastic surgery), podiatry, otolaryngology (e.g., ENT), gynecology (including laparoscopy), neurosurgery, orthopedics (e.g., soft tissue orthopedics), arthroscopy (e.g., knee arthroscopy), general and thoracic surgery (including open surgery and endoscopic surgery), dental and oral surgery, ophthalmology, genitourinary surgery, and veterinary surgery.

In some embodiments, $CO_2$ laser systems can be used in the ablation, vaporization, excision, incision, and/or coagulation of tissue (e.g., soft tissue) in dermatology and/or plastic surgery in the performance of laser skin resurfacing, laser derm-abrasion, and/or laser burn debridement. Laser skin resurfacing (e.g., by ablation and/or vaporization) can be performed, for example, in the treatment of wrinkles, rhytids, and/or furrows (including fine lines and texture irregularities). Laser skin resurfacing can be performed for the reduction, removal, and/or treatment of: keratoses (including actinic keratosis), seborrhoecae vulgares, seborrheic wart, and/or verruca seborrheica; vermillionectomy of the lip; cutaneous horns; solar/actinic elastosis; cheilitis (including actinic cheilitis); lentigines (including lentigo maligna or Hutchinson's malignant freckle); uneven pigmentation/dyschromia; acne scars; surgical scars; keloids (including acne keloidalis nuchae); hemangiomas (including Buccal, port wine and/or pyogenic granulomas/granuloma pyogenicum/ granuloma telagiectaticum); tattoos; telangiectasia; removal of skin tumors (including periungual and/or subungual fibromas); superficial pigmented lesions; adenosebaceous hypertrophy and/or sebaceous hyperplasia; rhinophyma reduction; cutaneous papilloma; milia; debridement of eczematous and/ or infected skin; basal and squamous cel carcinoma (including keratoacanthomas, Bowen's disease, and/or Bowenoid Papulosis lesions); nevi (including spider, epidermal, and/or protruding); neurofibromas; laser de-epithelialization; tricoepitheliomas; xanthelasma palpebrarum; and/or syringoma. $CO_2$ laser systems can be used for laser ablation, vaporization and/or excision for complete and/or partial nail matrixectomy, for vaporization and/or coagulation of skin lesions (e.g., benign and/or malignant, vascular and/or avascular), and/or for Moh's surgery, for lipectomy. Further examples include using laser system 1300 for laser incision and/or excision of soft tissue for the performance of upper and/or lower eyelid blepharoplasty, and/or for the creation of recipient sites for hair transplantation.

In certain embodiments, $CO_2$ laser systems is used in the laser ablation, vaporization, and/or excision of soft tissue during podiatry procedures for the reduction, removal, and/or treatment of: verrucae vulgares/plantar warts (including paronychial, periungual, and subungual warts); porokeratoma ablation; ingrown nail treatment; neuromas/fibromas (including Morton's neuroma); debridement of ulcers; and/or other soft tissue lesions. $CO_2$ laser systems can also be used for the laser ablation, vaporization, and/or excision in podiatry for complete and/or partial matrixectomy.

$CO_2$ laser systems can be used for laser incision, excision, ablation, and/or vaporization of soft tissue in otolaryngology for treatment of: choanal atresia; leukoplakia (including oral, larynx, uvula, palatal, upper lateral pharyngeal tissue); nasal obstruction; adult and/or juvenile papillomatosis polyps; polypectomy of nose and/or nasal passages; lymphangioma removal; removal of vocal cord/fold nodules, polyps and cysts; removal of recurrent papillomas in the oral cavity, nasal cavity, larynx, pharynx and trachea (including the uvula, palatal, upper lateral pharyngeal tissue, tongue and vocal cords); laser/tumor surgery in the larynx, pharynx, nasal, ear and oral structures and tissue; Zenker' diverticulum/pharynoesophageal diverticulum (e.g., endoscopic laser-assisted esophagodiverticulostomy); stenosis (including subglottic stenosis); tonsillectomy (including tonsillar cryptolysis, neoplasma) and tonsil ablation/tonsillotomy; pulmonary bronchial and tracheal lesion removal; benign and malignant nodules, tumors and fibromas (e.g., of the larynx, pharynx, trachea, tracheobronchial/endobronchial); benign and/or malignant lesions and/or fibromas (e.g., of the nose or nasal passages); benign and/or malignant tumors and/or fibromas (e.g., oral); stapedotomy/stapedectomy; acoustic neuroma in the ear; superficial lesions of the ear (including chondrodermatitis nondularis chronica helices/Winkler's disease); telangiectasia/hemangioma of larynx, pharynx, and/or trachea (including uvula, palatal, and/or upper lateral pharyngeal tissue); cordectomy, cordotomy (e.g., for the treatment of vocal cord paralysis/vocal fold motion impairment), and/or cordal lesions of larynx, pharynx, and/or trachea; myringotomy/tympanostomy (e.g., tympanic membrane fenestration); uvulopalatoplasty (e.g., LAUP); turbinectomy and/or turbinate reduction/ablation; septal spur ablation/reduction and/or septoplasty; partial glossectomy; tumor resection on oral, subfacial and/or neck tissues; rhinophyma; verrucae vulgares; and/or gingivoplasty/gingivectomy.

In some embodiments, $CO_2$ laser systems can be used for the laser incision, excision, ablation, and/or vaporization of soft tissue in gynecology for treatment of: conizaton of the cervix (including cervical intraepithelial neoplasia, vulvar and/or vaginal intraepithelial neoplasia); condyloma acuminata (including cervical, genital, vulvar, preineal, and/or Bowen's disease, and/or Bowenoid papulosa lesions); leukoplakia (e.g., vulvar dystrophies); incision and drainage of Bartholin's and/or nubuthian cysts; herpes vaporization; urethral caruncle vaporization; cervical dysplasia; benign and/or malignant tumors; and/or hemangiomas.

$CO_2$ laser systems can be used for the vaporization, incision, excision, ablation and/or coagulation of soft tissue in endoscopic and/or laparoscopic surgery, including gynecology laparoscopy, for treatment of: endometrial lesions (inclusing ablation of endometriosis); excision/lysis of adhesions; salpingostomy; oophorectomy/ovariectomy; fimbroplasty; metroplasty; tubal microsurgery; uterine myomas and/or fibroids; ovarian fibromas and/or follicle cysts; uterosacral ligament ablation; and/or hysterectomy.

In certain embodiments, $CO_2$ laser systems are used for the laser incision, excision, ablation, and/or vaporization of soft tissue in neurosurgery for the treatment of cranial conditions, including: posterior fossa tumors; peripheral neurectomy; benign and/or malignant tumors and/or cysts (e.g., gliomos, menigiomas, acoustic neuromas, lipomas, and/or large tumors); arteriovenous malformation; and/or pituitary gland tumors. In some embodiments, $CO_2$ laser systems are used for the laser incision, excision, ablation, and/or vaporization of soft tissue in neurosurgery for the treatment of spinal cord conditions, including: incision/excision and/or vaporization of benign and/or malignant tumors and/or cysts; intra- and/or extradural lesions; and/or laminectomy/laminotomy/microdisectomy.

$CO_2$ laser systems can be used for the incision, excision, and/or vaporization of soft tissue in orthopedic surgery in applications that include arthroscopic and/or general surgery. Arthroscopic applications include: menisectomy; chondromalacia; chondroplasty; ligament release (e.g., lateral ligament release); excision of plica; and/or partial synovectomy. General surgery applications include: debridement of traumatic wounds; debridement of decubitis and/or diabetic ulcers; microsurgery; artificial joint revision; and/or polymer (e.g., polymethylmethacrylate) removal.

$CO_2$ laser systems can also be used for incision, excision, and/or vaporization of soft tissue in general and/or thoracic surgery, including endoscopic and/or open procedures. Such applications include: debridement of decubitus ulcers, stasis, diabetic and other ulcers; mastectomy; debridement of burns; rectal and/or anal hemorrhoidectomy; breast biopsy; reduction mammoplasty; cytoreduction for metastatic disease; laparotomy and/or laparoscopic applications; mediastinal and/or thoracic lesions and/or abnormalities; skin tag vaporization; atheroma; cysts (including sebaceous cysts, pilar cysts, and/or mucous cysts of the lips); pilonidal cyst removal and/or repair; abscesses; and/or other soft tissue applications.

In certain embodiments, $CO_2$ laser systems can be used for the incision, excision, and/or vaporization of soft tissue in dentistry and/or oral surgery, including for: gingivectomy; gingivoplasty; incisional and/or excisional biopsy; treatment of ulcerous lesions (including aphthous ulcers); incision of infection when used with antibiotic therapy; frenectomy; excision and/or ablation of benign and/or malignant lesions; homeostasis; operculectomy; crown lengthening; removal of soft tissue, cysts, and/or tumors; oral cavity tumors and/or hemangiomas; abscesses; extraction site hemostasis; salivary gland pathologies; preprosthetic gum preparation; leukoplakia; partial glossectomy; and/or periodontal gum resection.

In some embodiments, $CO_2$ laser systems can be used for incision, excision, and/or vaporization of soft tissue in genitourinary procedures, including for: benign and/or malignant lesions of external genitalia; condyloma; phimosis; and/or erythroplasia.

A number of embodiments of the invention have been described. Nevertheless, it will be understood that various modifications may be made without departing from the spirit and scope of the invention. For example, while the conduits disclosed above are all two-part conduits, conduits composed of more than two portions (e.g., three portions, four portions, or more) may also be used. Accordingly, other embodiments are within the scope of the following claims.

The invention claimed is:

1. An apparatus, comprising:
a conduit configured to direct radiation at a wavelength λ from a light source to a target location of a patient, the conduit comprising:
a flexible optical waveguide extending along a waveguide axis, the flexible optical waveguide having a melting point less than 900 degrees C., having a hollow core and being configured to guide radiation at λ through the hollow core along the waveguide axis; and
a second optical waveguide extending along the waveguide axis, the second optical waveguide having an outer surface, having a hollow core, terminating in a distal tip having an open output end, and being coupled to the flexible optical waveguide to receive radiation from the flexible optical waveguide and to deliver radiation through the open output end to the target location, wherein the second optical waveguide is different from the flexible optical waveguide and has a melting point higher than the melting point of the flexible optical waveguide.

2. The apparatus of claim 1, wherein the flexible optical waveguide is adapted to guide the radiation to the target location while a portion of the flexible optical waveguide is bent through an angle of at least about 90 degrees and the portion has a radius of curvature of up to about 12 centimeters.

3. The apparatus of claim 2, wherein the radiation has an average power at the output end of at least about 1 Watt when the portion of the flexible optical waveguide is bent.

4. The apparatus of claim 3, wherein the radiation has an average power at the output end of at least about 5 Watts when the portion of the flexible optical waveguide is bent.

5. The apparatus of claim 2, wherein the flexible optical waveguide is adapted to guide the radiation to the target location when the portion of the flexible optical waveguide has a radius of curvature of up to about 10 centimeters.

6. The apparatus of claim 5, wherein the flexible optical waveguide is adapted to guide the radiation to the target location when the portion of the flexible optical waveguide has a radius of curvature of about 5 centimeters or less.

7. The apparatus of claim 1, wherein the waveguide axis includes a bent portion along the length of the second optical waveguide.

8. The apparatus of claim 1, wherein the bent portion of the second optical waveguide is adjustably bendable.

9. The apparatus of claim 1, wherein the second optical waveguide comprises a rigid waveguide.

10. The apparatus of claim 1, wherein the flexible optical waveguide and the second optical waveguide comprise different mechanical properties.

11. The apparatus of claim 10, wherein the second optical waveguide has a higher mechanical strength than the flexible optical waveguide.

12. The apparatus of claim 1, wherein the second optical waveguide comprises a dielectric tube having a metal coating.

13. The apparatus of claim 1, wherein the second optical waveguide is more rigid than the flexible optical waveguide.

14. The apparatus of claim 1, wherein the second optical waveguide is less rigid than the flexible optical waveguide.

15. The apparatus of claim 1, further comprising a light source configured to provide radiation at a wavelength λ.

16. The apparatus of claim 15, wherein the light source comprises a laser.

17. The apparatus of claim 1, wherein the hollow core of the second optical waveguide increases in diameter along its length from the coupling with the first flexible optical waveguide to the output end.

18. The apparatus of claim 1, wherein the outer surface of the second optical waveguide decreases in diameter along its length from the coupling with the first flexible optical waveguide to the output end.

19. The apparatus of claim 1, wherein the second optical waveguide comprises a ceramic tube.

20. The apparatus of claim 12, wherein the metal coating of the dielectric tube comprises a layer of a metal on an inner surface of the dielectric tube.

21. An apparatus, comprising:
a conduit configured to direct radiation at a wavelength λ from a light source to a target location of a patient, the conduit comprising:
a flexible optical waveguide extending along a waveguide axis, the flexible optical waveguide having a hollow core and being configured to guide radiation at λ through the hollow core along the waveguide axis; and a second optical waveguide extending along the waveguide axis, the second optical waveguide having an outer surface, having a hollow core, terminating in a distal tip having an open output end, and being coupled to the flexible optical waveguide to receive radiation from the flexible optical waveguide and to deliver radiation through the open output end to the target location, wherein the second optical waveguide is different from the flexible optical waveguide and has at least one of a different core diameter and a different outer diameter than the flexible optical waveguide;

wherein the flexible optical waveguide has a melting point less than 900degrees C. and the second optical waveguide has a melting point of at least 1,000 degrees C.

22. The apparatus of claim 21 wherein the hollow core of the second optical waveguide increases in diameter along its length from the coupling with the first flexible optical waveguide to the output end.

23. The apparatus of claim 21 wherein the outer surface of the second optical waveguide decreases in diameter along its length from the coupling with the first flexible optical waveguide to the output end.

24. The apparatus of claim 21 wherein the second optical waveguide comprises a ceramic tube.

25. The apparatus of claim 21 wherein the second optical waveguide comprises a dielectric tube having a metal coating.

* * * * *